US012594289B2

(12) United States Patent
Conlon et al.

(10) Patent No.: US 12,594,289 B2
(45) Date of Patent: *Apr. 7, 2026

(54) POTENTIATION OF ANTIBIOTIC EFFECT

(71) Applicant: The University of North Carolina at Chapel Hill, Chapel Hill, NC (US)

(72) Inventors: Brian Conlon, Durham, NC (US); Sarah Conlon, Durham, NC (US); Lauren Radlinski, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/448,538

(22) Filed: Aug. 11, 2023

(65) Prior Publication Data

US 2023/0381212 A1 Nov. 30, 2023

Related U.S. Application Data

(62) Division of application No. 16/630,174, filed as application No. PCT/US2018/042800 on Jul. 19, 2018, now abandoned.

(60) Provisional application No. 62/534,450, filed on Jul. 19, 2017.

(51) Int. Cl.
| | |
|---|---|
| *A61K 31/702* | (2006.01) |
| *A61K 47/26* | (2006.01) |
| *A61P 31/04* | (2006.01) |

(52) U.S. Cl.
CPC ............ *A61K 31/702* (2013.01); *A61K 47/26* (2013.01); *A61P 31/04* (2018.01)

(58) Field of Classification Search
CPC ........ A61K 31/20–201; A61K 31/7004; A61K 31/7016; A61K 31/7028; A61K 31/7034; A61K 31/7036; A61K 47/26; A61K 2300/00; A61P 31/00–04
See application file for complete search history.

(56) References Cited

U.S. PATENT DOCUMENTS

| | | | | |
|---|---|---|---|---|
| 5,855,913 A | * | 1/1999 | Hanes ................... | A61K 31/135 424/501 |
| 2004/0147595 A1 | | 7/2004 | Kjelleberg et al. | |
| 2006/0228384 A1 | | 10/2006 | Eldridge | |
| 2009/0032427 A1 | | 2/2009 | Cheu et al. | |
| 2011/0257115 A1 | | 10/2011 | Leighton | |
| 2013/0089598 A1 | * | 4/2013 | Gupta ................... | A61K 31/375 424/450 |
| 2014/0228312 A1 | | 8/2014 | Zhang et al. | |

FOREIGN PATENT DOCUMENTS

| | | | |
|---|---|---|---|
| WO | 9508344 A1 | 3/1995 | |
| WO | 2010067245 A1 | 6/2010 | |

OTHER PUBLICATIONS

Mugabe, C. et al."Mechanism of enhanced activity of liposome-entrapped aminoglycosides . . . " Antimicrob. Agents Chemother., vol. 50, No. 6, pp. 2016-2022. (Year: 2006).*

Krause, K. et al "Aminoglycosides: an overview" Cold Spring Harb. Persp. Med., vol. 6, pp. 1-18. (Year: 2016).*

Hess, D. et al "Antibacterial synergy of glycerol monolaurate and aminoglycosides . . . " Antimicrob. Agens Chemother., vol. 58, No. 11, pp. 6970-6973. (Year: 2014).*

Park, S. et al "Fatty acids as aminoglycoside antibiotic adjuvants . . . " Frontiers Microbiol., vol. 13, pp. 1-9. (Year: 2022).*

Lee, Food Control 80 (2017) 74-82. (Year: 2017).*

Saraiva, Eur. J. Lipid Sci. Technol. 2011, 113, 967-972. (Year: 2011).*

"International Preliminary Report on Patentability corresponding to International Application No. PCT/US2018/042800 mailed Jan. 30, 2020".

"International Search Report and Written Opinion corresponding to International Application No. PCT/US2018/042800 mailed Oct. 25, 2018".

Chan, Ben C.L, et al., "Combating against methicillin-resistant *Staphylococcus aureus*—two fatty acids from Purslane (*Portulaca oleracea* L.) exhibit synergistic effects with erythromycin", J. Pharm. Pharmacol. 67(1):107-116 (Jul. 27, 2014).

Coutinho, Henrique D.M, et al., "Potentiating Effect of Mentha arvensis and Chlorpromazine in the Resistance to Aminoglycosides of Methicillin Resistant *Staphylococcus aureus*", In Vivo 23:287-290 (2009).

Desbois, Andrew P, et al., "Antibacterial Activity of Long-Chain Polyunsaturated Fatty Acids against Propionibacterium acnes and *Staphylococcus aureus*", Mar. Drugs 11:4544-4557 (Nov. 13, 2013).

Doern, Christopher D, "When Does 2 Plus 2 Equal 5? A Review of Antimicrobial Synergy Testing", J. Clin. Microbiol. 52(12):4124-4128 (Jun. 11, 2014).

Inès, Mnif, et al., "Glycolipid biosurfactants: potential related biomedical and biotechnological applications", Carbohyd. Res. 416:59-69 (Jul. 31, 2015).

Oliveira, O. P, et al., "Antimicrobial activity and chemical composition of fixed oil extracted from the body fat of a snake Spilotes pullatus", Pharm. Biol. 52(6):740-744 (Feb. 21, 2014).

Rivardo, Fabrizio, et al., "Synergistic effect of lipopeptide biosurfactant with antibiotics against *Escherichia coli* CTF073 biofilm", International Journal of Antimicrobial Agents 37:324-331 (2011).

Saravanakumari, et al., ""Structural characterization of a novel xylolipid biosurfactant from Lactococcus lactis and analysis of antibacterial activity against multi-drug resistant pathogens", Bioresource Technology 101:8851-8854 (2010)".

(Continued)

*Primary Examiner* — Layla D Berry

(74) *Attorney, Agent, or Firm* — Myers Bigel, P.A.

(57) ABSTRACT

The present invention relates to compositions, kits and methods using combinations of surfactants or cell wall-hydrolyzing enzymes with antibiotics to potentiate the antibiotic effect against bacterial infections. In some embodiments, the surfactant is a pore-forming biosurfactant such as rhamnolipids and the antibiotic is an aminoglycoside antibiotic such as tobramycin.

18 Claims, 15 Drawing Sheets

(56)     References Cited

OTHER PUBLICATIONS

Varjani, et al., ""Carbon spectrum utilization by an indigenous strain of Pseudomonas aeruginosa NCIM 5514: Production, characterization and surface active properties of biosurfactant", Bioresource Technology 221:510-516 (2016)".

Varvaresou, A, et al., "Biosurfactants in cosmetics and biopharmaceuticals", Letters in Applied Microbiology 61:214-223 (Apr. 25, 2015).

Wille, J. J, et al., "Palm itoleic Acid Isomer (C16 :1 A6) in Human Skin Sebum Is Effective against Gram-Positive Bacteria", Skin Pharmacol. Appl. Skin Physiol. 16:176-187 (May/Jun. 2003).

Papadopoulou, et al., "Overcoming biological barriers to improve treatment of a Staphylococcus aureus wound infection", Cell Chemical Biology 30:513-526 (May 18, 2023).

* cited by examiner

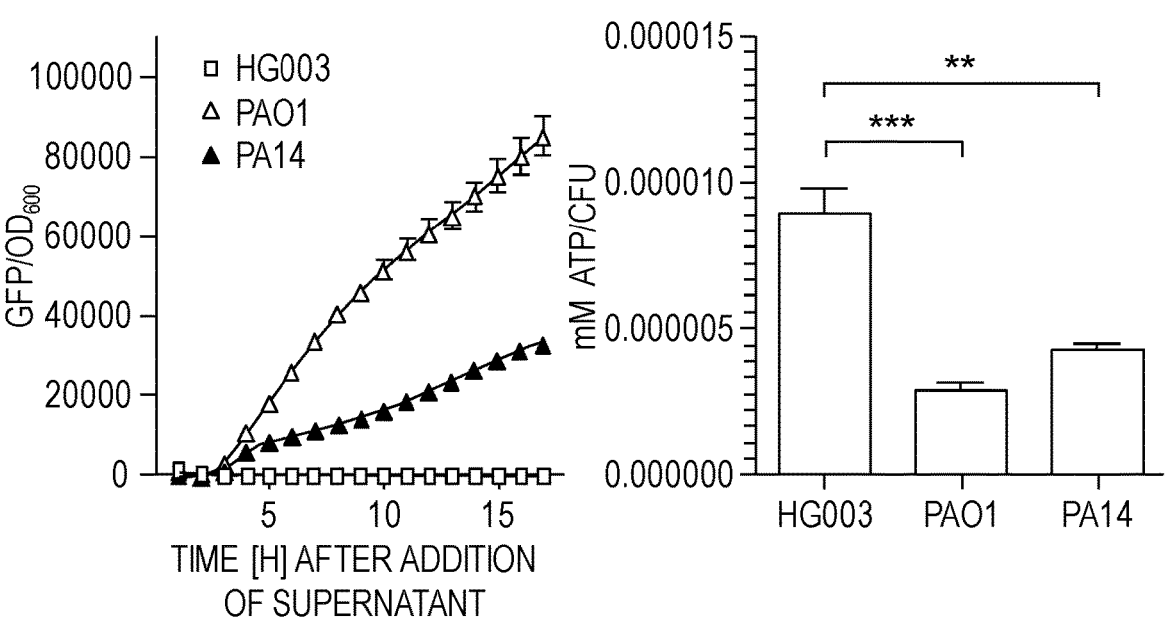
Figure 2A
Figure 2B
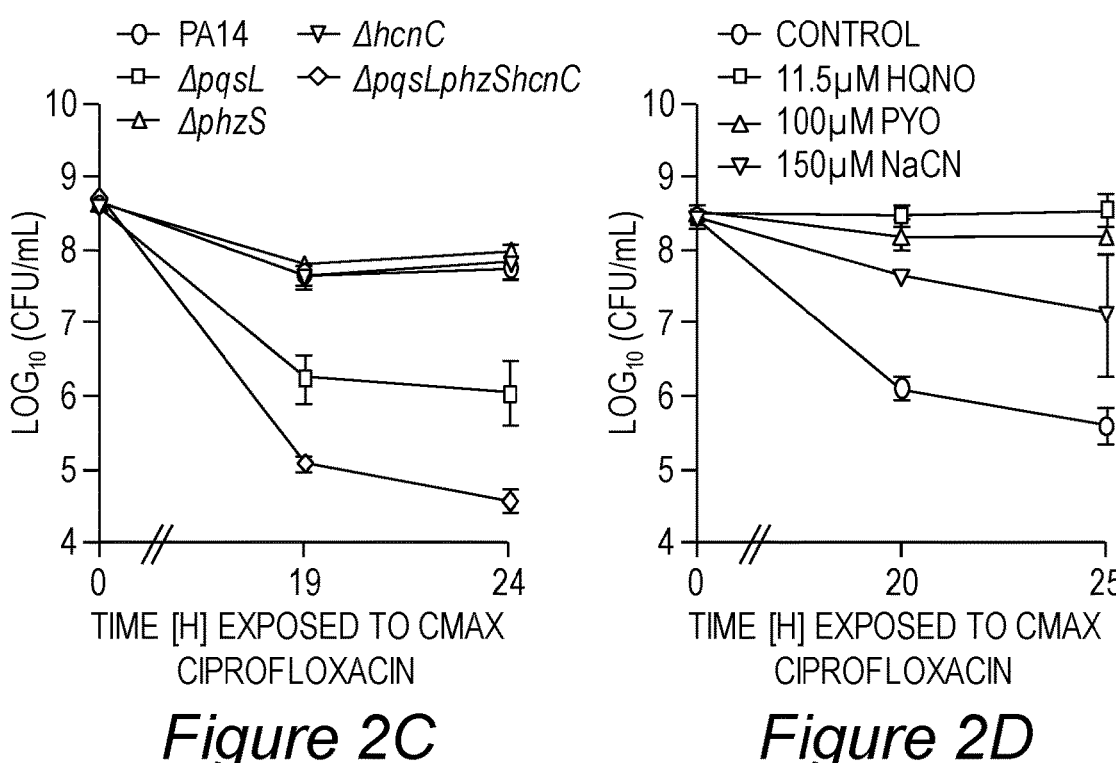
Figure 2C
Figure 2D

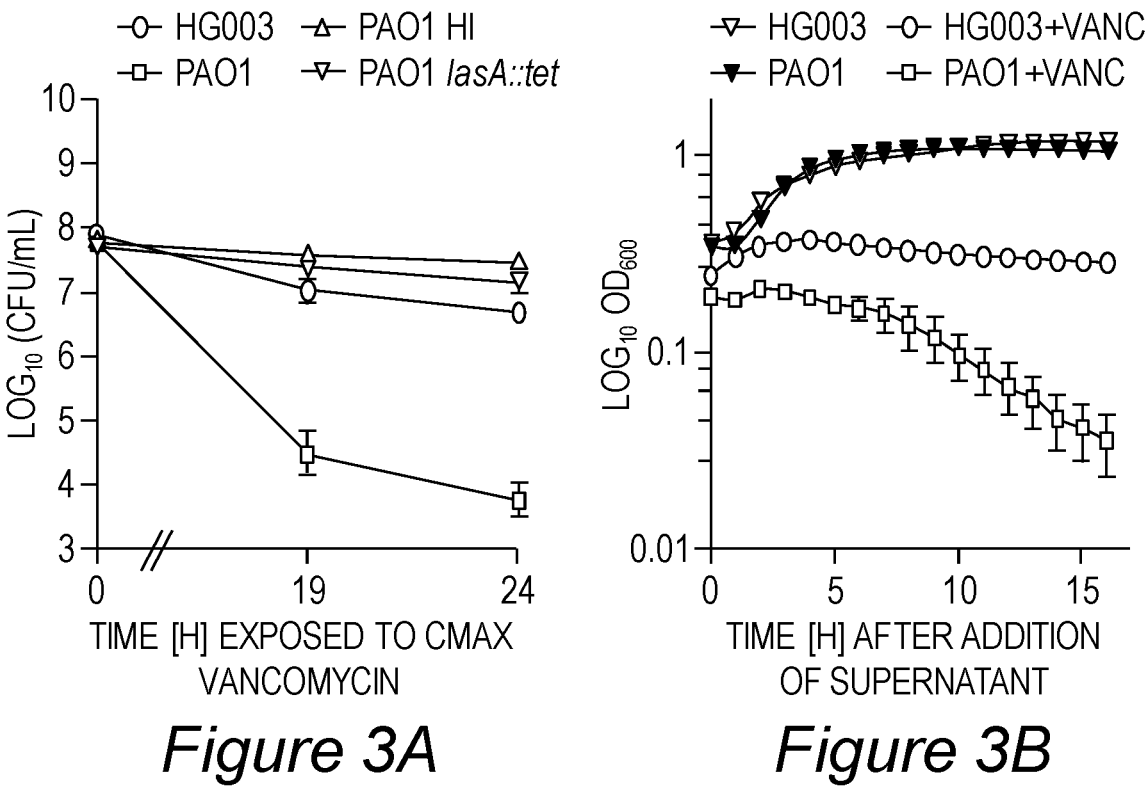
*Figure 3A*
*Figure 3B*
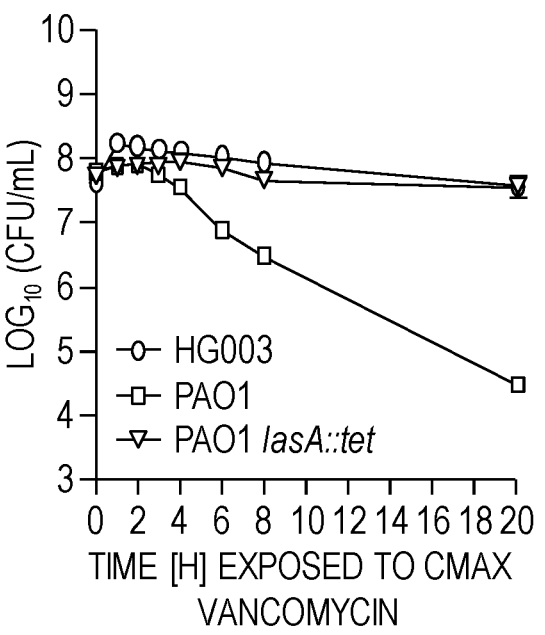
*Figure 3C*

POTENTIATION OF ANTIBIOTIC EFFECT

STATEMENT OF PRIORITY

This application is a divisional of U.S. patent application Ser. No. 16/630,174, filed Jan. 10, 2020, which is a 35 U.S.C. § 371 national phase application of PCT Application PCT/US2018/042800 filed Jul. 19, 2018, which claims the benefit of U.S. Provisional Application Ser. No. 62/534,450, filed Jul. 19, 2017, the entire contents of which are incorporated by reference herein.

STATEMENT OF GOVERNMENT SUPPORT

This invention was made with government support under AI125501 and AI137273 awarded by the National Institutes of Health. The government has certain rights in the invention.

FIELD OF THE INVENTION

The present invention relates to compositions, kits and methods using combinations of surfactants or cell wall-hydrolyzing enzymes with antibiotics to potentiate the antibiotic effect against bacterial infections.

BACKGROUND OF THE INVENTION

*Staphylococcus aureus* is a major human pathogen responsible for numerous chronic and relapsing infections. These infections often fail to respond to antibiotic treatment, even in the apparent absence of antibiotic resistance. Additionally, antibiotic resistance of microorganisms such as *S. aureus* is a growing dilemma worldwide. The overuse of currently available antibiotics has contributed to this issue. The development of new antibiotics and alternative methods of treating infections is needed.

There remains a need for compounds and combinations of compounds that can increase the sensitivity of bacteria to antibiotics and treat bacterial infections.

SUMMARY OF THE INVENTION

The present invention is based, in part, on the development of effective combinations of surfactants or cell wall-hydrolyzing enzymes and other antibiotics that enhance the activity of the other antibiotics and increase the antibiotic sensitivity of bacteria.

Accordingly, one aspect of the invention relates to a composition comprising a surfactant and an aminoglycoside antibiotic.

Another aspect of the invention relates to a kit comprising a surfactant and an aminoglycoside antibiotic.

Another aspect of the invention relates to a method of increasing the sensitivity of a bacteria to an aminoglycoside antibiotic, comprising contacting the bacteria with an effective amount of a surfactant and the aminoglycoside antibiotic.

Another aspect of the invention relates to a method of treating a bacterial infection in a subject in need thereof, comprising administering to the subject a therapeutically effective amount of a surfactant and the aminoglycoside antibiotic.

Another aspect of the invention relates to a method of reducing the risk of recurrence of a bacterial infection in a subject in need thereof, comprising administering to the subject having a bacterial infection a therapeutically effective amount of a surfactant and the aminoglycoside antibiotic.

Another aspect of the invention relates to a method of disrupting a biofilm, comprising contacting the biofilm with an effective amount of a surfactant and the aminoglycoside antibiotic.

Another aspect of the invention relates to a composition comprising a cell wall-hydrolyzing enzyme and a cell wall synthesis inhibitor glycopeptide antibiotic.

Another aspect of the invention relates to a kit comprising a cell wall-hydrolyzing enzyme and a cell wall synthesis inhibitor glycopeptide antibiotic.

Another aspect of the invention relates to a method of increasing the sensitivity of a bacteria to a cell wall synthesis inhibitor, comprising contacting the bacteria with an effective amount of a cell wall-hydrolyzing enzyme and the cell wall synthesis inhibitor glycopeptide antibiotic.

Another aspect of the invention relates to a method of treating a bacterial infection in a subject in need thereof, comprising administering to the subject a therapeutically effective amount of a cell wall-hydrolyzing enzyme and a cell wall synthesis inhibitor glycopeptide antibiotic.

Another aspect of the invention relates to a method of reducing the risk of recurrence of a bacterial infection in a subject in need thereof, comprising administering to the subject having a bacterial infection a therapeutically effective amount of a cell wall-hydrolyzing enzyme and a cell wall synthesis inhibitor glycopeptide antibiotic.

Another aspect of the invention relates to a method of disrupting a biofilm, comprising contacting the biofilm with an effective amount of a cell wall-hydrolyzing enzyme and a cell wall synthesis inhibitor glycopeptide antibiotic.

These and other aspects of the invention are set forth in more detail in the description of the invention below.

BRIEF DESCRIPTION OF THE DRAWINGS

FIGS. 2A-2D show *P. aeruginosa* secondary metabolites inhibit *S. aureus* aerobic respiration resulting in a drop in intracellular ATP. (A) *S. aureus* strain HG003 harboring plasmid PpflB::gfp, was grown to mid-exponential phase and treated with *P. aeruginosa* PAO1 supernatant, PA14 supernatant or *S. aureus* HG003 supernatant for 30 min. OD600 and gn, expression levels were determined using a Biotek Synergy H1 microplate reader. (B) Intracellular ATP was measured after 1.5 h incubation with supernatant. $p < 0.001$, *$p < 0.0005$ (Student's t-test). (C) *S. aureus* strain HG003 was grown to mid-exponential phase in MHB media and pre-treated with sterile supernatants from *P. aeruginosa* strains PA14 wild-type or its isogenic mutants or (D) clinically relevant concentrations of HQNO, pyocyanin (PYO) or sodium cyanide (NaCN) for 30 min prior to antibiotic challenge. At indicated times, an aliquot was washed and plated to enumerate survivors. All experiments were performed in biological triplicate. Error bars represent mean±sd.

FIGS. 3A-3C show *P. aeruginosa* supernatant potentiates killing by vancomycin via the LasA endopeptidase. *S. aureus* HG003 was grown to mid-exponential phase and exposed to sterile supernatants for 30 min prior to addition of vancomycin 50 μg/ml. Where indicated, PA14 supernatant was heat inactivated (PA14 HI) at 95° C. for 10 min. (A, C) At indicated times, an aliquot was removed, washed and plated to enumerate survivors or (B) 100 μl cells were added to a 96-well plate and lysis was measured at $OD_{600}$ every hr for 16 h. All experiments were performed in biological triplicate. Error bars represent mean±sd.

DETAILED DESCRIPTION OF THE INVENTION

Figure 1A:
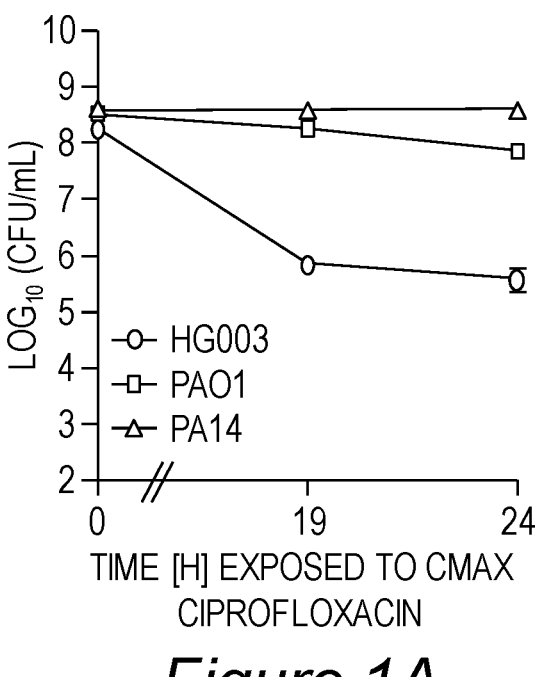
FIGS. 1A-1D show *P. aeruginosa* supernatant alters *S. aureus* antibiotic susceptibility. *S. aureus* strain HG003 was grown to mid-exponential phase and pre-treated with sterile supernatant from either *P. aeruginosa* PAO1, PA14 or *S. aureus* HG003 for 30 min. Cultures were then challenged with the C. of (A) ciprofloxacin (B) oxacillin (C) vancomycin or (D), tobramycin. At indicated times, an aliquot from each culture was washed and plated to enumerate survivors. All experiments were performed in biological triplicate. Error bars represent mean±sd.

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

Amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of polypeptide, dose, time, temperature, enzymatic activity or other biological activity and the like, is meant to encompass variations of ±10%, ±5%, ±1%, ±0.5%, or even ±0.1% of the specified amount.

The transitional phrase "consisting essentially of" means that the scope of a claim is to be interpreted to encompass the specified materials or steps recited in the claim, and those that do not materially affect the basic and novel characteristics of the claimed invention.

The term "modulate," "modulates," or "modulation" refers to enhancement (e.g., an increase) or inhibition (e.g., a decrease) in the specified level or activity.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectable activity (at most, an insignificant amount, e.g., less than about 10% or even 5%).

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

By the terms "treat," "treating," or "treatment of," it is intended that the severity of the subject's condition is reduced or at least partially improved or modified and that some alleviation, mitigation or decrease in at least one clinical symptom is achieved.

A "synergistic" effect, as used herein, is an effect that is greater than additive when two molecules are administered to a subject simultaneously or sequentially.

The term "therapeutic index," as used herein, refers to the ratio of the dose of drug that causes adverse effects at an incidence/severity not compatible with the targeted indication (e.g., toxic dose in 50% of subjects, TD50) to the dose that leads to the desired pharmacological effect (e.g., efficacious dose in 50% of subjects, ED50). A widening of the therapeutic index refers to an increase in the difference between the toxic and therapeutic dose.

The term "antibiotic-resistant," as used herein, refers to the ability of a microorganism to resist the toxic effects of an antibiotic, usually due to a mutation. Resistance typically occurs when the microorganism produces a protein that disables an antibiotic or prevents transport of the antibiotic into the cell. As used herein, the term also includes microorganisms that undergo reversal of tolerance. An antibiotic-resistant microorganism is one in which the minimum inhibitory concentration (MIC) is increased by at least 10% relative to the average MIC of the non-resistant strain.

The term "antibiotic-tolerant," as used herein, refers to phenotypic variants of a microorganism produced stochastically in a population, which are non-growing, dormant cells and therefore tolerant of antibiotics.

The term "minimum inhibitory concentration (MIC)" refers to the lowest concentration of a compound or molecule that prevents visible growth of a bacterium.

The term "sequentially" refers to the administration of two or more agents one after the other and close enough in time that each of the agents exerts a biological activity on the other agent, e.g., the two or more agents have an effect in combination.

One aspect of the invention relates to a composition comprising a surfactant and an aminoglycoside antibiotic. The composition may comprise more than one aminoglycoside antibiotic, e.g., 1, 2, 3, 4, or 5 or more aminoglycoside antibiotics. The composition may comprise more than one surfactant, e.g., 1, 2, 3, 4, or 5 or more surfactants. The composition may be a pharmaceutical composition comprising a surfactant and an aminoglycoside antibiotic together with a pharmaceutically acceptable carrier.

In some embodiments, the surfactant is a membrane-modifying surfactant, i.e., one that modifies the cell membrane to allow increased penetration of an aminoglycoside antibiotic. In some embodiments, the surfactant is a pore-forming biosurfactant (i.e., a naturally occurring molecule that is capable of forming a pore in a cell membrane). In some embodiments, the pore-forming biosurfactant may be a biosurfactant from a bacteria, e.g., a *Lactobacillus* spp. or *Streptococcus* spp., e.g., *L. casei, L. lactis, L. fermentus* RC 14, or *S. thermophilus* A. In some embodiments, the pore-forming biosurfactant may be a rhamnolipid, a xylolipid, or any combination thereof. The rhamnolipid may be from *Pseudomonas aeruginosa*. In some embodiments, the rhamnolipid may be a mono-rhamnolipid, a di-rhamnolipid, or a combination thereof. Rhamnolipids are a class of glycolipid that have a glycosyl head group, in this case a rhamnose moiety, and a 3-(hydroxyalkanoyloxy)alkanoic acid (HAA) fatty acid tail, such as 3-hydroxydecanoic acid. There are two main classes of rhamnolipids: mono-rhamnolipids and di-rhamnolipids, which consist of one or two rhamnose groups respectively. In some embodiments, the rhamnolipids are predominantly mono-rhamnolipids or di-rhamnolipids, e.g., at least 70%, 75%, 80%, 85%, 90%, or more of mono-rhamnolipids or di-rhamnolipids. In some embodiments, the rhamnolipids have 1 or 2 fatty acid tails that are predominantly C10 or C12, e.g., at least 70%, 75%, 80%, 85%, 90%, or more C10 or C12.

Surfactants (or surface-active substances) that may be present are anionic, non-ionic, cationic and/or amphoteric surfactants. Typical examples of anionic surfactants include, but are not limited to, soaps, alkylbenzenesulfonates, alkanesulfonates, olefin sulfonates, alkyl ether sulfonates, glycerol ether sulfonates, α-methyl ester sulfonates, sulfo fatty acids, alkyl sulphates, fatty alcohol ether sulphates, glycerol ether sulphates, fatty acid ether sulphates, hydroxy mixed ether sulphates, monoglyceride (ether) sulphates, fatty acid amide (ether) sulphates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, e.g., acyl lactylates, acyl tartrates, acyl glutamates and acyl aspartates, alkyl oligo-glucoside sulphates, protein fatty acid condensates (in particular wheat-based vegetable products) and alkyl (ether) phosphates. Examples of non-ionic surfactants include, but are not limited to, fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolysates (in particular wheat-based vegetable products), polyol fatty acid esters, sugar esters, sorbitan esters, polysorbates and amine oxides. Examples of amphoteric or zwitterionic surfactants include, but are not limited to, alkylbetaines, alkylamidobetaines, aminopropionates, aminoglycinates, imidazolinium-betaines and sulfobetaines.

In some embodiments, the surfactant can be fatty alcohol polyglycol ether sulphates, monoglyceride sulphates, mono- and/or dialkyl sulfosuccinates, fatty acid isethionates, fatty acid sarcosinates, fatty acid taurides, fatty acid glutamates, alpha-olefinsulfonates, ether carboxylic acids, alkyl oligoglucosides, fatty acid glucamides, alkylamidobetaines, amphoacetals and/or protein fatty acid condensates.

Examples of zwitterionic surfactants include betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethyl-carboxymethyl glycinate.

In some embodiments, the surfactant can be a nioniogenic surfactant selected from the following: the addition products of from 2 to 30 mole of ethylene oxide and/or 0 to 5 mole of propylene oxide onto linear fatty alcohols having 8 to 22 carbon atoms, onto fatty acids having 12 to 22 carbon atoms, onto alkylphenols having 8 to 15 carbon atoms in the alkyl group, or onto alkylamines having 8 to 22 carbon atoms in the alkyl radical; alkyl and/or alkenyl oligoglycosides having 8 to 22 carbon atoms in the alk(en)yl radical and the ethoxylated analogs thereof; the addition products of from 1 to 15 mole of ethylene oxide onto castor oil and/or hydrogenated castor oil; the addition products of from 15 to 60 mole of ethylene oxide onto castor oil and/or hydrogenated castor oil; partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mole of ethylene oxide; partial esters of polyglycerol (average degree of self-condensation 2 to 8), trimethylolpropane, pentaerythritol, sugar alcohols (e.g., sorbitol), alkyl glucosides (e.g., methyl glucoside, butyl glucoside, lauryl glucoside), and polyglucosides (e.g., cellulose) with saturated and/or unsaturated, linear or branched fatty acids having 12 to 22 carbon atoms and/or hydroxycarboxylic acids having 3 to 18 carbon atoms, and the adducts thereof with 1 to 30 mole of ethylene oxide; mixed esters of pentaerythritol, fatty acids, citric acid and fatty alcohols and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof; wool wax alcohols; polysiloxane-polyalkylpolyether copolymers and corresponding derivatives; and block copolymers, e.g., polyethylene glycol-30 dipolyhydroxystearates.

In some embodiments, the surfactant is a polyalkylene glycol such as, for example, polyethylene glycol or polypropylene glycol. In some embodiments, the surfactant is polyethylene glycol having a molecular weight 100 Da to 5,000 Da, 200 Da to 2,500 Da, 300 Da to 1,000 Da, 400 Da to 750 Da, 550 Da to 650 Da, or about 600 Da.

In some embodiments, the surfactant is a poloxamer.

In some embodiments, the surfactant is composed of one or more fatty alcohols. In some embodiments, the fatty alcohol is a linear or branched C6 to C35 fatty alcohol. Examples of fatty alcohols include, but are not limited to, capryl alcohol (1-octanol), 2-ethyl hexanol, pelargonic alcohol (1-nonanol), capric alcohol (1-decanol, decyl alcohol), undecyl alcohol (1-undecanol, undecanol, hendecanol), lauryl alcohol (dodecanol, 1-dodecanol), tridecyl alcohol (1-tridecanol, tridecanol, isotridecanol), myristyl alcohol (1-tetradecanol), pentadecyl alcohol (1-pentadecanol, pentadecanol), cetyl alcohol (1-hexadecanol), palmitoleyl alcohol (cis-9-hexadecen-1-ol), heptadecyl alcohol (1-n-heptadecanol, heptadecanol), stearyl alcohol (1-octadecanol), isostearyl alcohol (16-methylheptadecan-1-ol), elaidyl alcohol (9E-octadecen-1-ol), oleyl alcohol (cis-9-octadecen-1-ol), linoleyl alcohol (9Z,12Z-octadecadien-1-ol), elaidolinoleyl alcohol (9E,12E-octadecadien-1-ol), linolenyl alcohol (9Z,12Z,15Z-octadecatrien-1-ol) elaidolinolenyl alcohol (9E,12E,15-E-octadecatrien-1-ol), ricinoleyl alcohol (12-hydroxy-9-octadecen-1-ol), nonadecyl alcohol (1-nonadecanol), arachidyl alcohol (1-eicosanol), heneicosyl alcohol (1-heneicosanol), behenyl alcohol (1-docosanol), erucyl alcohol (cis-13-docosen-1-ol), lignoceryl alcohol (1-tetracosanol), ceryl alcohol (1-hexacosanol), montanyl alcohol, cluytyl alcohol (1-octacosanol), myricyl alcohol, melissyl alcohol (1-triacontanol), geddyl alcohol (1-tetratriacontanol), or cetearyl alcohol.

In some embodiments, the surfactant is a fatty acid, e.g., palmitoleic acid or glycerol monolaureate.

The aminoglycoside antibiotic may be any aminoglycoside antibiotic known to be therapeutically effective or which may be therapeutically effective when combined with the surfactant. In some embodiments, the aminoglycoside antibiotic is streptomycin, kanamycin A, amikacin, tobramycin, dibekacin, gentamicin, sisomicin, netilmicin, neomycin B, neomycin C, neomycin E (paromomycin), or any combination thereof. In some embodiments, the aminoglycoside antibiotic is tobramycin.

The composition may be a dosage form, e.g., a unit dosage form. In some embodiments, the surfactant and aminoglycoside antibiotic are both present in therapeutically effective amounts. In some embodiments, the surfactant and aminoglycoside antibiotic are both present in synergistic amounts, e.g., amounts that, when administered to a subject, will produce a synergistic effect.

In certain embodiments, the surfactant and/or aminoglycoside antibiotic is present in a sub-therapeutic amount (i.e., an amount that does not provide antimicrobial activity) but produces a therapeutic effect in combination. In some embodiments, the surfactant and/or aminoglycoside antibiotic is present in an amount that, by itself, is not therapeutic but renders a third antibiotic therapeutically effective.

Another aspect of the invention relates to a kit comprising a surfactant and an aminoglycoside antibiotic as discussed above. The kit may comprise the surfactant and aminoglycoside antibiotic in the same container or in separate containers.

Another aspect of the invention relates to a method of increasing the sensitivity of a bacteria to an aminoglycoside antibiotic, comprising contacting the bacteria with an effective amount of a surfactant and the aminoglycoside antibiotic.

An additional aspect of the invention relates to a method of treating a bacterial infection in a subject in need thereof, comprising administering to the subject a therapeutically effective amount of a surfactant and an aminoglycoside antibiotic.

Another aspect of the invention relates to a method of reducing the risk of recurrence of a bacterial infection in a subject in need thereof, comprising administering to the subject having a bacterial infection a therapeutically effective amount of a surfactant and an aminoglycoside antibiotic.

Another aspect of the invention relates to a method of disrupting a biofilm, comprising contacting the biofilm with an effective amount of a surfactant and an aminoglycoside antibiotic.

In each of the methods of the invention, the surfactant and the aminoglycoside antibiotic may be administered simultaneously, e.g., in the same dosage form or in separate dosage forms. In each of the methods of the invention, the surfactant and the aminoglycoside antibiotic may be administered sequentially, but close enough together in time to exert a biological effect on each other. In each of the methods of the invention, the surfactant and the aminoglycoside antibiotic may be administered in synergistic amounts.

In each of the methods of the invention, the surfactant may decrease the minimum inhibitory concentration of the aminoglycoside antibiotic, e.g., by at least about 5%, 10%, 20%, 30%, 40%, 50%, 60%, 70%, 80%, or 90%.

In some embodiments, the surfactant is administered before the aminoglycoside antibiotic. In other embodiments, the aminoglycoside antibiotic is administered before the surfactant. The second molecule may be administered at any effective time point after the first molecule is administered, e.g., about 1, 2, 3, 4, 5, 6, 7, 8, 9, 10, 15, 20, 25, 30, 35, 40, 45, 55, or 60 minutes or about 1.5, 2, 3, 4, 5, 6, 7, 8, 9, 10, 11, or 12 hours after the first molecule is administered.

In certain embodiments of the methods of the invention, the subject is one that has been diagnosed as being infected with antibiotic-resistant or antibiotic-tolerant bacteria or is suspected of being infected with antibiotic-resistant or antibiotic-tolerant bacteria. The subject may not have been previously treated for the infection. The subject may be administered the surfactant first to prime the subject for aminoglycoside antibiotic treatment.

In some embodiments, the subject has been treated with an aminoglycoside antibiotic and the treatment has been ineffective (e.g., the infection has not been reduced, has been reduced but not eradicated, or was thought to have been eradicated but has returned). The surfactant may be added to the treatment with the same aminoglycoside antibiotic or with a different aminoglycoside antibiotic.

In some embodiments, the subject may be immunocompromised or otherwise have diminished ability to fight the infection.

The methods of the present invention may permit the surfactant and/or the aminoglycoside antibiotic to be administered at a dose that would not be therapeutically effective if administered alone. The MIC of surfactant and/or aminoglycoside antibiotic when provided together may be decreased by at least about 5%, e.g., at least about 10%, 15%, 20%, 25%, 30%, 35%, 40%, 45%, 50%, or more relative to the MIC of either agent alone.

Another aspect of the invention relates to a composition comprising a cell wall-hydrolyzing enzyme and a cell wall synthesis inhibitor glycopeptide antibiotic. The composition may comprise more than one cell wall synthesis inhibitor glycopeptide antibiotic, e.g., 1, 2, 3, 4, or 5 or more cell wall synthesis inhibitor glycopeptide antibiotics. The composition may comprise more than one cell wall-hydrolyzing enzyme, e.g., 1, 2, 3, 4, or 5 or more cell wall-hydrolyzing enzymes.

In some embodiments, the cell wall-hydrolyzing enzyme may be LasA protease, lysostaphin, an autolysin, or any combination thereof. In certain embodiments, the cell wall-hydrolyzing enzyme is LasA protease.

In some embodiments, the cell wall synthesis inhibitor glycopeptide antibiotic may be any cell wall synthesis inhibitor glycopeptide antibiotic known to be therapeutically effective or which may be therapeutically effective when combined with the cell wall-hydrolyzing enzyme. In some embodiments, the aminoglycoside antibiotic is may be vancomycin, teicoplanin, telavancin, ramoplanin, decaplanin, oritavancin, dalbavancin, or any combination thereof. In certain embodiments, the cell wall synthesis inhibitor glycopeptide antibiotic is vancomycin.

The composition may be a dosage form, e.g., a unit dosage form. In some embodiments, the cell wall-hydrolyzing enzyme and cell wall synthesis inhibitor glycopeptide antibiotic are both present in therapeutically effective amounts. In some embodiments, the cell wall-hydrolyzing enzyme and cell wall synthesis inhibitor glycopeptide antibiotic are both present in synergistic amounts, e.g., amounts that, when administered to a subject, will produce a synergistic effect.

In certain embodiments, the cell wall-hydrolyzing enzyme and/or cell wall synthesis inhibitor glycopeptide antibiotic is present in an amount that, by itself, is not therapeutic but produces a therapeutic effect in combination. In some embodiments, the cell wall-hydrolyzing enzyme and/or cell wall synthesis inhibitor glycopeptide antibiotic is present in an amount that, by itself, is not therapeutic but renders a third antibiotic therapeutically effective.

Another aspect of the invention relates to a kit comprising a cell wall-hydrolyzing enzyme and a cell wall synthesis inhibitor glycopeptide antibiotic as discussed above. The kit may comprise the cell wall-hydrolyzing enzyme and cell wall synthesis inhibitor glycopeptide antibiotic in the same container or in separate containers.

Another aspect of the invention relates to a method of increasing the sensitivity of a bacteria to a cell wall synthesis inhibitor glycopeptide antibiotic, comprising contacting the bacteria with an effective amount of a cell wall-hydrolyzing enzyme and the cell wall synthesis inhibitor glycopeptide antibiotic.

An additional aspect of the invention relates to a method of treating a bacterial infection in a subject in need thereof, comprising administering to the subject a therapeutically effective amount of a cell wall-hydrolyzing enzyme and a cell wall synthesis inhibitor glycopeptide antibiotic.

Another aspect of the invention relates to a method of reducing the risk of recurrence of a bacterial infection in a subject in need thereof, comprising administering to the subject having a bacterial infection a therapeutically effective amount of a cell wall-hydrolyzing enzyme and a cell wall synthesis inhibitor glycopeptide antibiotic.

Another aspect of the invention relates to a method of disrupting a biofilm, comprising contacting the biofilm with an effective amount of a cell wall-hydrolyzing enzyme and a cell wall synthesis inhibitor glycopeptide antibiotic.

In each of the methods of the invention, the cell wall-hydrolyzing enzyme and the cell wall synthesis inhibitor glycopeptide antibiotic may be administered simultaneously, e.g., in the same dosage form or in separate dosage forms. In each of the methods of the invention, the cell wall-hydrolyzing enzyme and the cell wall synthesis inhibitor glycopeptide antibiotic may be administered sequentially, but close enough together in time to exert a biological effect on each other. In each of the methods of the invention, the cell wall-hydrolyzing enzyme and the cell wall synthesis inhibitor glycopeptide antibiotic may be administered in synergistic amounts.

In each of the methods of the invention, the cell wall-hydrolyzing enzyme may decrease the minimum inhibitory concentration of the cell wall synthesis inhibitor glycopeptide antibiotic.

In some embodiments, the cell wall-hydrolyzing enzyme is administered before the cell wall synthesis inhibitor glycopeptide antibiotic. In other embodiments, the cell wall synthesis inhibitor glycopeptide antibiotic is administered before the cell wall-hydrolyzing enzyme. The second molecule may be administered at any effective time point after the first molecule is administered, e.g., about 1, 2, 3, 4, 5, 6, 7, 8, 9, 10, 15, 20, 25, 30, 35, 40, 45, 50, or 60 minutes or about 1.5, 2, 3, 4, 5, 6, 7, 8, 9, 10, 11, or 12 hours after the first molecule is administered.

In certain embodiments of the methods of the invention, the subject is one that has been diagnosed as being infected with antibiotic-resistant or antibiotic-tolerant bacteria or is suspected of being infected with antibiotic-resistant or antibiotic-tolerant bacteria. The subject may not have been previously treated for the infection. The subject may be administered the cell wall-hydrolyzing enzyme first to prime the subject for cell wall synthesis inhibitor glycopeptide antibiotic treatment.

In some embodiments, the subject has been treated with a cell wall synthesis inhibitor glycopeptide antibiotic and the treatment has been ineffective (e.g., the infection has not been reduced, has been reduced but not eradicated, or was thought to have been eradicated but has returned). The cell wall-hydrolyzing enzyme may be added to the treatment with the same cell wall synthesis inhibitor glycopeptide antibiotic or with a different cell wall synthesis inhibitor glycopeptide antibiotic.

In some embodiments, the subject may be immunocompromised or otherwise have diminished ability to fight the infection.

The methods of the present invention may permit the cell wall-hydrolyzing enzyme and/or the cell wall synthesis inhibitor glycopeptide antibiotic to be administered at a dose that that would not be therapeutically effective if administered alone. The MIC of the cell wall-hydrolyzing enzyme and/or cell wall synthesis inhibitor glycopeptide antibiotic when provided together may be decreased by at least about 5%, e.g., at least about 10%, 15%, 20%, 25%, 30%, 35%, 40%, 45%, 50%, or more relative to the MIC of either agent alone.

The microorganism, e.g., bacteria, treated by the present invention may be any microorganism known in the art. In some embodiments, the microorganism is an antibiotic-resistant or antibiotic-tolerant strain. In certain embodiments, the bacteria is a gram-negative bacteria. In certain embodiments, the bacteria is a gram-positive bacteria, e.g., *Staphylococcus aureus*, e.g., methicillin-resistant *Staphylococcus aureus*. Pathogenic bacteria and other microorganisms include, but are not limited to, *Rickettsia, Chlamydia, Mycobacteria, Clostridia, Corynebacteria, Mycoplasma,*

*Ureaplasma, Legionella, Shigella, Salmonella*, pathogenic *Escherichia coli* species, *Bordatella, Neisseria, Treponema, Bacillus, Haemophilus, Moraxella, Vibrio, Staphylococcus* spp., *Streptococcus* spp., *Campylobacter* spp., *Borrelia* spp., *Leptospira* spp., *Erlichia* spp., *Klebsiella* spp., *Pseudomonas* spp., *Helicobacter* spp., and any other pathogenic microorganism now known or later identified (see, e.g., Microbiology, Davis et al, Eds., 4$^{th}$ ed., Lippincott, New York, 1990, the entire contents of which are incorporated herein by reference for the teachings of pathogenic microorganisms). Specific examples of microorganisms include, but are not limited to, *Helicobacter pylori, Chlamydia pneumoniae, Chlamydia trachomatis, Ureaplasma urealyticum, Mycoplasma pneumoniae, Staphylococcus aureus, Streptococcus pyogenes, Streptococcus pneumoniae, Streptococcus viridans, Enterococcus faecalis, Neisseria meningitidis, Neisseria gonorrhoeae, Treponema pallidum, Bacillus anthracis, Salmonella typhi, Vibrio cholera, Pasteurella pestis (Yersinia pestis), Pseudomonas aeruginosa, Campylobacter jejuni, Clostridium difficile, Clostridium botulinum, Mycobacterium tuberculosis, Borrelia burgdorferi, Haemophilus ducreyi, Corynebacterium diphtheria, Bordetella pertussis, Bordetella parapertussis, Bordetella bronchiseptica, Haemophilus influenza*, and enterotoxic *Escherichia coli*. In some embodiments, the bacteria is *Staphylococcus aureus*. In some embodiments, the bacteria is methicillin-resistant *Staphylococcus aureus*. In certain embodiments, the bacteria may be gram-negative bacteria or gram-positive bacteria.

In certain embodiments, the surfactant and aminoglycoside antibiotic or the cell wall-hydrolyzing enzyme and cell wall synthesis inhibitor glycopeptide antibiotic of the invention are administered directly to a subject. In some embodiments, the compounds will be suspended in a pharmaceutically-acceptable carrier (e.g., physiological saline) and administered orally or by intravenous infusion, or administered subcutaneously, intramuscularly, intrathecally, intraperitoneally, intrarectally, intravaginally, intranasally, intragastrically, intratracheally, or intrapulmonarily. In another embodiment, the intratracheal or intrapulmonary delivery can be accomplished using a standard nebulizer, jet nebulizer, wire mesh nebulizer, dry powder inhaler, or metered dose inhaler. The agents can be delivered directly to the site of the disease or disorder, such as lungs, kidney, or intestines. The dosage required depends on the choice of the route of administration; the nature of the formulation; the nature of the patient's illness; the subject's size, weight, surface area, age, and sex; other drugs being administered; and the judgment of the attending physician. Suitable dosages for each agent are in the range of 0.01-100.0 μg/kg. Wide variations in the needed dosage are to be expected in view of the variety of antibiotics available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2-, 3-, 4-, 6-, 8-, 10-; 20-, 50-, 100-, 150-, or more fold). Encapsulation of the surfactant and aminoglycoside antibiotic or the cell wall-hydrolyzing enzyme and cell wall synthesis inhibitor glycopeptide antibiotic in a suitable delivery vehicle (e.g., polymeric microparticles or implantable devices) may increase the efficiency of delivery, particularly for oral delivery.

As a further aspect, the invention provides pharmaceutical formulations and methods of administering the same to achieve any of the therapeutic effects (e.g., treatment of infection) discussed above. The pharmaceutical formulation may comprise any of the reagents discussed above in a pharmaceutically acceptable carrier.

By "pharmaceutically acceptable" it is meant a material that is not biologically or otherwise undesirable, i.e., the material can be administered to a subject without causing any undesirable biological effects such as toxicity.

The formulations of the invention can optionally comprise medicinal agents, pharmaceutical agents, carriers, adjuvants, dispersing agents, diluents, and the like.

The compounds of the invention can be formulated for administration in a pharmaceutical carrier in accordance with known techniques. See, e.g., Remington, *The Science And Practice of Pharmacy* (21$^{st}$ Ed. 2006). In the manufacture of a pharmaceutical formulation according to the invention, the compound (including the physiologically acceptable salts thereof) is typically admixed with, inter alia, an acceptable carrier. The carrier can be a solid or a liquid, or both, and is preferably formulated with the compound as a unit-dose formulation, for example, a tablet, which can contain from 0.01 or 0.5% to 95% or 99% by weight of the compound. One or more compounds can be incorporated in the formulations of the invention, which can be prepared by any of the well-known techniques of pharmacy.

The formulations of the invention include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and inhalation administration, administration to the liver by intraportal delivery, as well as direct organ injection (e.g., into the liver, into the brain for delivery to the central nervous system, or into the pancreas) or injection into a body cavity. The most suitable route in any given case will depend on the nature and severity of the condition being treated and on the nature of the particular compound which is being used.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the compound can be administered in solid dosage forms, such as capsules, tablets, and powders, or in liquid dosage forms, such as elixirs, syrups, and suspensions. Compounds can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the compound, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising a compound of the invention, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 1 mg to about 10 grams of the compound or salt. When the compound or salt is substantially water-insoluble, a sufficient amount of emulsifying agent which is pharmaceutically acceptable can be employed in sufficient quantity to emulsify the compound or salt in an aqueous carrier. One such useful emulsifying agent is phosphatidyl choline.

Formulations suitable for rectal administration are preferably presented as unit dose suppositories. These can be prepared by admixing the compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, Tyle, *Pharm. Res.* 3:318 (1986)) and typically take the form of an optionally buffered aqueous solution of the compounds. Suitable formulations comprise citrate or bis/tris buffer (pH 6) or ethanol/water and contain from 0.1 to 0.2M of the compound.

The compound can alternatively be formulated for nasal administration or otherwise administered to the lungs of a subject by any suitable means, e.g., administered by an aerosol suspension of respirable particles comprising the compound, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the compound can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the compound can likewise be produced with any solid particulate medicament aerosol generator, by techniques known in the pharmaceutical art.

Alternatively, one can administer the compound in a local rather than systemic manner, for example, in a depot or sustained-release formulation.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same can be incorporated into lipid vesicles. In such an instance, due to the water solubility of the compound or salt, the compound or salt will be substantially entrained within the hydrophilic center or core of the liposomes. The lipid layer employed can be of any conventional composition and can either contain cholesterol or can be cholesterol-free. When the compound or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations containing the compounds disclosed herein or salts thereof, can be lyophilized to produce a lyophilizate which can be reconstituted with a pharmaceutically acceptable carrier, such as water, to regenerate a liposomal suspension.

In the case of water-insoluble compounds, a pharmaceutical composition can be prepared containing the water-insoluble compound, such as for example, in an aqueous base emulsion. In such an instance, the composition will contain a sufficient amount of pharmaceutically acceptable emulsifying agent to emulsify the desired amount of the compound. Particularly useful emulsifying agents include phosphatidyl cholines and lecithin.

In particular embodiments, the compound is administered to the subject in a therapeutically effective amount, as that term is defined above. Dosages of pharmaceutically active compounds can be determined by methods known in the art, see, e.g., *Remington's Pharmaceutical Sciences* (Maack Publishing Co., Easton, Pa). The therapeutically effective dosage of any specific compound will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the compound, including the cases where a salt is employed. Toxicity concerns at the higher level can restrict intravenous dosages to a lower level such as up to about 10 mg/kg, with all weights being calculated based upon the weight of the compound, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Particular dosages are about 1 $\mu$mol/kg to 50 $\mu$mol/kg, and more particularly to about 22 $\mu$mol/kg and to 33 $\mu$mol/kg of the compound for intravenous or oral administration, respectively.

In particular embodiments of the invention, more than one administration (e.g., two, three, four, or more administrations) can be employed over a variety of time intervals (e.g., hourly, daily, weekly, monthly, etc.) to achieve therapeutic effects.

The present invention finds use in veterinary and medical applications. Suitable subjects include both avians and mammals, with mammals being preferred. The term "avian" as used herein includes, but is not limited to, chickens, ducks, geese, quail, turkeys, and pheasants. The term "mammal" as used herein includes, but is not limited to, humans, bovines, ovines, caprines, equines, felines, canines, lagomorphs, etc. Human subjects include neonates, infants, juveniles, and adults.

The present invention is more particularly described in the following examples that are intended as illustrative only since numerous modifications and variations therein will be apparent to those skilled in the art.

Example 1

Interspecies Interaction Determines *S. aureus* Antibiotic Susceptibility

*Staphylococcus aureus* is a major human pathogen responsible for numerous chronic and relapsing infections. These infections often fail to respond to antibiotic treatment, even in the apparent absence of antibiotic resistance. *S. aureus* frequently co-exists with the opportunistic pathogen *Pseudomonas aeruginosa* in burns, chronic wounds and the cystic fibrosis lung. Here, it is demonstrated that interaction with *P. aeruginosa* alters antibiotic susceptibility of *S. aureus* through a number of distinct pathways. At physiologically relevant concentrations, *P. aeruginosa* secondary metabolite 2-heptyl-4-hydroxyquinoline N-oxide (HQNO) induces tolerance of *S. aureus* to multiple antibiotics classes through respiratory inhibition and reduction of cellular ATP levels. Conversely, the *P. aeruginosa* bacteriolytic enzyme LasA potentiates killing and lysis of *S. aureus* by vancomycin. Furthermore, *P. aeruginosa* rhamnolipids facilitate the proton-motive force-independent uptake of tobramycin, promoting eradication of *S. aureus* persister populations. It was found here that the overall ability of *P. aeruginosa* to alter *S. aureus* antibiotic susceptibility is dependent on the production of HQNO, LasA and rhamnolipids, all of which are highly variable among clinical isolates examined. These findings demonstrate that antibiotic susceptibility is dependent not only on the genotype of the pathogen being targeted, but also on that of co-infecting microorganisms in the infection environment.

Accurate prediction of antimicrobial efficacy is essential for successful treatment of bacterial infection. Here it is shown that a single interspecies interaction between *S. aureus* and *P. aeruginosa* can completely transform the antibiotic susceptibility profile of *S. aureus*. Through multiple distinct mechanisms, *P. aeruginosa* can antagonize or potentiate the efficacy of multiple classes of antibiotics against *S. aureus*. Further, it is shown that the capacity of *P. aeruginosa* to alter antibiotic susceptibility of *S. aureus* is highly variable in clinical isolates. This work suggests that the efficacy of antibiotic treatment in polymicrobial infection is determined on the community level with interspecies interactions playing an important and as yet unappreciated role.

Materials and Methods

Bacterial strains and growth conditions. *S. aureus* strain HG003 was cultured aerobically in Mueller-Hinton broth (MHB) at 37° C. with shaking at 225 rpm. For anaerobic growth, overnight cultures were washed twice with PBS and diluted into 5 ml of pre-warmed (37° C.) TSB+100 mM MOPS (pH 7) to an $OD_{600}$ of 0.05. Cultures were prepared in triplicate in 16×150 mm glass tubes containing 1 mm stir bars. Following dilution, cultures were immediately transferred into a Coy anaerobic chamber and grown at 37° C. with stirring. *P. aeruginosa* strains were grown aerobically in MHB at 37° C. with shaking at 225 rpm. Burn wound isolates represent the first positive Pseudomonal wound cultures obtained from 5 unique patients admitted to the NC Jaycee Burn Center with a total body surface area burn ≥20% and/or inhalational injury after obtaining informed consent. Cystic fibrosis isolates were collected from 5 patients at the UNC medical center. Isolates were cultured from sputum or bronchoalveolar lavage (BAL) from patients with cystic fibrosis after obtaining informed consent.

Antibiotic survival assays. To prepare sterile supernatants, *S. aureus* and *P. aeruginosa* strains were grown in MHB at 37° C. with shaking at 225 rpm for ~20 h. The cultures were pelleted and supernatants were passed through a 0.2 µm filter. HG003 was grown to ~5×10⁷ (for cell wall acting antibiotics) or ~2×10⁸ cfu/ml (for all other antibiotics) in 3 ml MHB under aerobic conditions or in 5 ml TSB+100 mM MOPS under anaerobic conditions. Cells were pre-treated with 0.5 ml sterile supernatant (or 0.83 ml for anaerobic cultures) and returned to the incubator for a further 30 min. An aliquot was plated to enumerate cfu before the addition of antibiotics. Antibiotics were added at concentrations similar to the Cmax in humans at recommended dosing; ciprofloxacin 2.34 µg/ml, tobramycin 58 µg/ml, oxacillin 50 µg/ml, vancomycin 50 µg/ml. Ciprofloxacin concentration was increased to 4.68 µg/ml when cells were grown in TSB+100 mM MOPS to account for any decrease in pH where ciprofloxacin killing activity is reduced. At indicated times, an aliquot was removed and washed with 1% NaCl. Cells were serially diluted and plated to enumerate survivors. Where indicated sterile supernatant was heat-inactivated at 95° C. for 10 min before addition to culture. Where indicated, pyocyanin 100 µM, HQNO 11.5 µM, sodium cyanide 150 µM or rhamnolipids 10-50 µg/ml (50/50 mix of mono- and di-rhamnolipids, Sigma) were added in place of supernatant. Concentrations of respiratory toxins represent levels detected in the sputum of cystic fibrosis patients.

Promoter induction measurement. *S. aureus* strain HG003 harboring gn) promoter plasmid PpflB::gfp) were grown to ~2×10⁸ cfu/ml in 3 ml MHB containing chloramphenicol 10 µg/ml. Cultures were treated with 0.5 ml supernatant from HG003, PAO1, PA14 or *P. aeruginosa* clinical isolates as indicated. 200 µl culture was added to the wells of a clear bottom, black side 96-well plate. The plate was placed in a Biotek Synergy H1 microplate reader at 37° C. with shaking. Absorbance ($OD_{600}$) and GFP fluorescence (emission 528 nm and excitation 485 nm) were measured every 1 h for 16 h. GFP values were divided by $OD_{600}$.

ATP assays. HG003 was grown to ~2×10⁸ cfu/ml in 3 ml MHB and pre-treated with 0.5 ml sterile supernatant from *S. aureus* HG003 or *P. aeruginosa* PAO1 or PA14. ATP levels of the cultures were measured after 1.5 h as described previously using a Promega BacTiter Glo kit according to the manufacturer's instructions. P-values are indicated.

Vancomycin lysis assay. HG003 was grown to ~2×10⁸ cfu/ml in 3 ml MHB and pre-treated with 0.5 ml sterile supernatant from *S. aureus* HG003, *P. aeruginosa* PAO1, PA14 or *P. aeruginosa* clinical isolates as indicated. Cells were incubated for a further 30 min before addition of vancomycin 50 µg/ml. 200 µl aliquots were added to the wells of a clear 96-well plate and placed in a Biotek Synergy H1 microplate reader. Absorbance ($OD_{600}$) was measured every 1 h for 16 h.

Tobramycin-Texas Red Uptake. Tobramycin-Texas Red was made as described previously. *S. aureus* strain HG003 was grown to mid-exponential phase and then incubated with or without 30 µg/ml rhamnolipids for 30 min. Cells were plated to enumerate cfu prior to addition of Texas-Red tobramycin at a final concentration of 58 µg/ml. After 1 h, an aliquot of cells was removed, washed twice in 1% NaCl and plated to enumerate survivors. The remaining aliquot was analyzed for Texas Red uptake on a BD Fortessa flow cytometer. 30,000 events were recorded. Figures were generated using FSC Express 6 Flow.

Western blot analysis of LasA. *P. aeruginosa* strains were grown in MHB media for ~20 h. Cultures were normalized to $OD_{600}$ 2.0, pelleted and supernatants were passed through a 0.2 µm filter. Supernatants were boiled in SDS-sample buffer and run on a 4-12% bis-tris acrylamide gel (Invitrogen). Protein was transferred onto a PVDF membrane and LasA was detected using rabbit polyclonal anti-LasA antibodies (LifeSpan BioSciences, Inc.).

Staphylolytic assay. Staphylolytic assay was modified from Grande et al. Stationary phase *S. aureus* strain HG003 was heat killed at 95° C. for 20 min. Cells were pelleted and resuspended in 20 mM Tris-HCl (pH 8.0) at an $OD_{595}$ 0.8-1. *P. aeruginosa* strains were cultured in MHB media for ~20 h. Cultures were normalized to $OD_{600}$ 2.0, pelleted and supernatants were passed through a 0.2 µm filter. 17 µl sterile supernatant was added to 100 µl heat-killed cells. $OD_{595}$ was measured at time 0 and after 2 h and % cell lysis was determined. The values shown represent the average of biological triplicates.

Rhamnolipid Quantification. *P. aeruginosa* rhamnolipid production was quantified utilizing a drop collapse assay, as previously described. Briefly, clarified supernatants from overnight cultures of *P. aeruginosa* strains were serially diluted (1:1) with de-ionized water plus 0.005% crystal violet for visualization. 25 µl aliquots of each dilution were spotted on to the underside of a Petri dish plate and tilted to a 90° angle. Surfactant scores represent the reciprocal of the highest dilution at which a collapsed drop migrated down the surface of the plate.

Minimum inhibitory concentration (MIC) assays. MICs were determined using the microdilution method. Briefly, ~5×10⁵ cfu were incubated with varying concentrations of ciprofloxacin, tobramycin, oxacillin or vancomycin in a total volume of 200 µl MHB in a 96-well plate. Where indicated, 34 µl MHB was replaced with sterile *P. aeruginosa* or *S. aureus* supernatant or purified rhamnolipids at a final concentration of 10-50 µg/ml. MICs were determined following incubation at 37° C. for 24 h.

Results

Figure 1B:
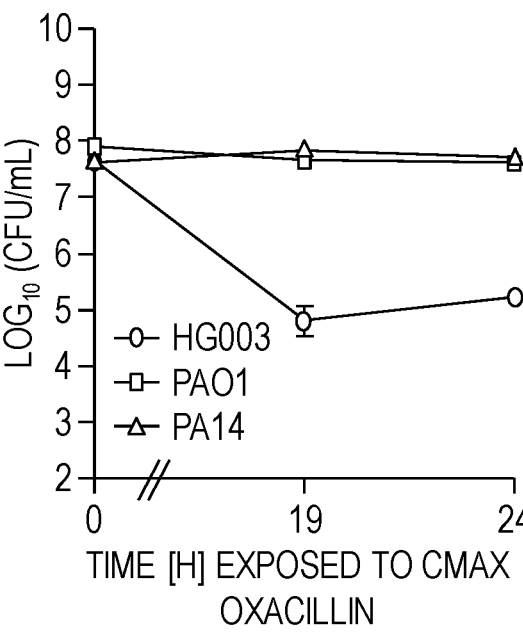
Figure 1C:
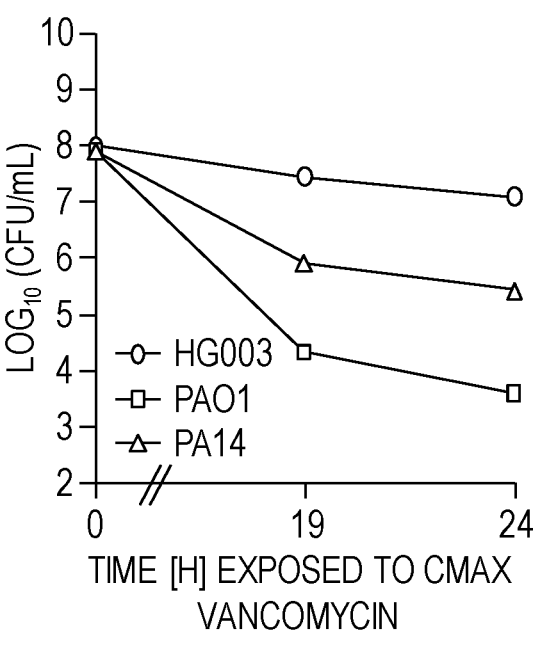

*P. aeruginosa* Supernatant Alters *S. aureus* Susceptibility to Antibiotic Killing Co-infections of *P. aeruginosa* and *S. aureus* within chronic wounds and the CF lung are generally more virulent and/or more difficult to treat than infections caused by either pathogen alone. The potential impact of this interspecies interaction on antibiotic susceptibility of *S. aureus* was analyzed. Cultures of *S. aureus* HG003 were grown to exponential phase and treated with sterile supernatants from *P. aeruginosa* PAO1, *P. aeruginosa* PA14 or *S. aureus* HG003 (control) overnight cultures for 30 minutes. Cultures were then challenged with various bactericidal antibiotics at physiologically relevant concentrations. It was found that *P. aeruginosa* PA01 or PA14 supernatant induced full tolerance of the population to ciprofloxacin—a fluoroquinolone and oxacillin—a β-lactam. This is in stark contrast to *S. aureus* supernatant treated control cultures, wherein at least 99% of the cells were killed by the antibiotic (FIGS. 1A and 1B). Interestingly, *P. aeruginosa* supernatant did not protect *S. aureus* from vancomycin killing. On the contrary, the presence of PA14 or PAO1 supernatant during vancomycin challenge resulted in a 2- and 4-log increase in cell death, respectively, relative to the *S. aureus* supernatant control (FIG. 1C). Minimum inhibitory concentration (MIC) assays were performed in the presence and absence of *P. aeruginosa* supernatant, and the MIC of oxacillin, vancomycin and ciprofloxacin were not affected by the presence of *P. aeruginosa*, demonstrating the phenotype is associated with tolerance but not resistance (Table 1).

The presence of *P. aeruginosa* has been associated with increased aminoglycoside resistance in *S. aureus*. MIC assays confirmed that *P. aeruginosa* supernatant induces an 8-fold increase in tobramycin resistance in *S. aureus*. Paradoxically, *P. aeruginosa* supernatant did not confer protection against tobramycin killing (Table 1, FIG. 1D). Together, these data highlight the complex influence *P. aeruginosa* exerts on antibiotic susceptibility of *S. aureus*.

*P. aeruginosa* Induces Multidrug Tolerance in *S. aureus* Through Respiratory Inhibition The bactericidal activity of many major classes of antibiotics is dependent on the activity of ATP-dependent processes including cell wall biosynthesis, DNA replication, transcription and translation. Low intracellular ATP concentrations lead to decreased activity of these pathways resulting in less antibiotic-induced damage and increased antibiotic tolerance. It was previously shown that the presence of *P. aeruginosa* pushes *S. aureus* towards fermentative mode of growth, even under aerobic conditions. To test this, the fermentation-specific promoter for pyruvate acetyltransferase (pflB) was cloned from *S. aureus* upstream of gfp in a low-copy plasmid. It was found that pflB expression is induced in *S. aureus* in response to *P. aeruginosa* supernatant (FIG. 2A). Fermentation is a far less efficient pathway for ATP production, yielding 2 ATP molecules for every glucose molecule metabolized, compared to the 32 ATP per glucose generated through aerobic respiration. Direct intracellular ATP quantification of cultures treated with *P. aeruginosa* or *S. aureus* supernatant revealed that *P. aeruginosa* supernatant induces significant depletion of *S. aureus* intracellular ATP (FIG. 2B).

*P. aeruginosa* secondary metabolites pyocyanin, HCN and HQNO inhibit the *S. aureus* electron transport chain, thereby inhibiting aerobic respiration. Furthermore, culture of *S. aureus* in the presence of purified HQNO results in increased resistance to tobramycin. It was reasoned that these respiratory toxins may be responsible for inducing a low ATP, antibiotic tolerant state in *S. aureus* during exposure to *P. aeruginosa* supernatant. To investigate this possibility, we created mutants in genes pqsL, phzS and hcnC in PA14. These mutants are incapable of producing HQNO, pyocyanin and hydrogen cyanide, respectively. It was found that mutation of pqsL (HQNO negative) drastically reduced the capacity of the supernatant to induce *S. aureus* antibiotic tolerance suggesting conditions tolerance to ciprofloxacin is primarily mediated by HQNO (FIG. 2C). Double (FIG. 7A) and triple mutants (FIG. 2C) deficient in the biosynthesis of HQNO, pyocyanin and hydrogen cyanide were constructed. Although deletion of pqsL has the most dramatic effect on the ability of *P. aeruginosa* to induce tolerance in *S. aureus*, a ΔpqsLphzShcnC triple mutant was further reduced in its ability to confer protection to antibiotic killing (FIG. 2C). The ability of *P. aeruginosa* supernatant to induce antibiotic tolerance in *S. aureus* under anaerobic conditions was examined. As expected, no protection from antibiotic killing was observed following pre-treatment with PA14 supernatant during anoxic growth in the absence of a terminal electron acceptor (FIG. 7B), supporting the conclusion that *P. aeruginosa*-mediated induction of *S. aureus* antibiotic tolerance is due to the inhibition of *S. aureus* respiration.

Figures 7A, 7B, 7C, 7D, 7E:
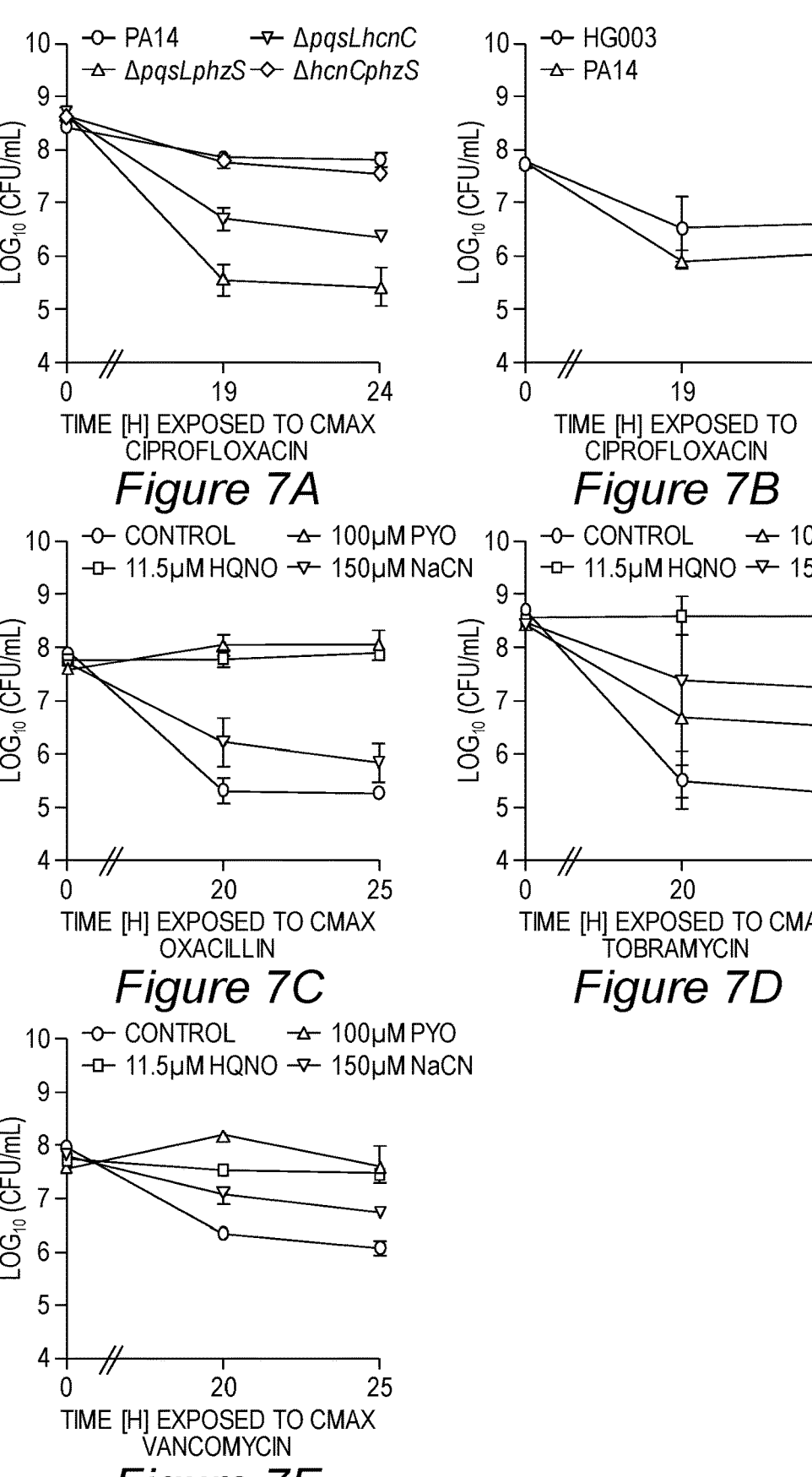
FIGS. 7A-7E show *S. aureus* strain HG003 was grown to mid-exponential phase in MHB media and pre-treated with (A) sterile supernatants from *P. aeruginosa* strains PA14 wild-type or its isogenic mutants or (C-E) clinically relevant concentrations of HQNO, pyocyanin (PYO) or sodium cyanide (NaCN) for 30 min prior to antibiotic challenge. (B) HG003 was grown to mid-exponential phase in TSB+100 mM MOPS in an anaerobic chamber and pre-treated with sterile supernatants from HG003 or PA14 for 30 min before addition of ciprofloxacin. At indicated times, an aliquot was washed and plated to enumerate survivors. All experiments were performed in biological triplicate. Error bars represent mean±sd.

Next, exponential phase *S. aureus* cultures were exposed to concentrations of HQNO, pyocyanin or cyanide previously detected in the sputum of cystic fibrosis patients with active *P. aeruginosa* infection, then challenged these cultures with antibiotics. It was found that all three compounds were capable of inducing tolerance of *S. aureus* to ciprofloxacin (FIG. 2D). Similar levels of tolerance were observed for oxacillin, tobramycin and vancomycin, with HQNO inducing the most robust tolerance to antibiotic killing (FIGS. 7C-7E).

*P. aeruginosa* LasA Endopeptidase Potentiates Vancomycin Bactericidal Activity Against *S. aureus*

The presence of purified HQNO, pyocyanin or NaCN confers protection to *S. aureus* against all antibiotics tested, including vancomycin. However, it was observed that *P. aeruginosa* supernatant significantly potentiates vancomycin killing of *S. aureus* (FIG. 1C). It was reasoned that *P. aeruginosa* supernatant must contain one or more additional factors that dominate the protective influence of *P. aeruginosa* respiratory toxins. Heat-inactivated PAO1 supernatant failed to potentiate vancomycin killing of *S. aureus* cultures, implicating an extracellular protein in the phenotype (FIG. 3A). The potentiation of vancomycin killing was accompanied by total lysis of the culture over time (FIG. 3B). Importantly, no lysis was observed for cells treated with *P. aeruginosa* supernatant in the absence of vancomycin (FIG. 3B). Due to the lytic nature of the killing, LasA, an endopeptidase produced by *P. aeruginosa*, which was previously shown to attack the cell wall of *S. aureus* during in vivo competition, became of interest. The capacity of supernatant from a lasA mutant in PAO1 to synergize with vancomycin was examined. Interestingly, it was found that no significant killing by vancomycin occurred under these conditions compared to a 3-log reduction in *S. aureus* cfu in the presence of the PAO1 wild-type supernatant (FIGS. 3A and 3C). It appears that the combination of vancomycin inhibition of peptidoglycan cross-linking and LasA cleavage of pentaglycine cross-bridges results in extensive cell lysis and a potent bactericidal effect. Expression of LasA has been observed in clinical *P. aeruginosa* isolates, and the protein itself has been detected in the sputum of cystic fibrosis patients. These findings suggest that LasA production by *P. aeruginosa* may be an important determinant of vancomycin efficacy against *S. aureus* during the treatment of co-infections.

*P. aeruginosa* Rhamnolipids Increase Tobramycin Uptake and Efficacy Against *S. aureus*

Figure 1D:
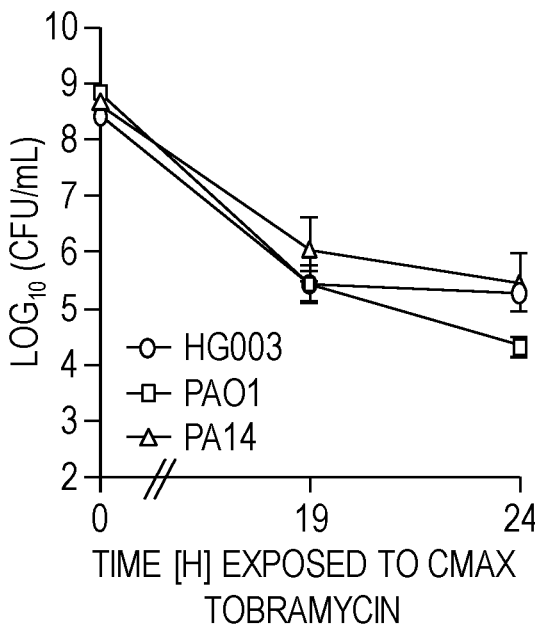
Figure 4A:
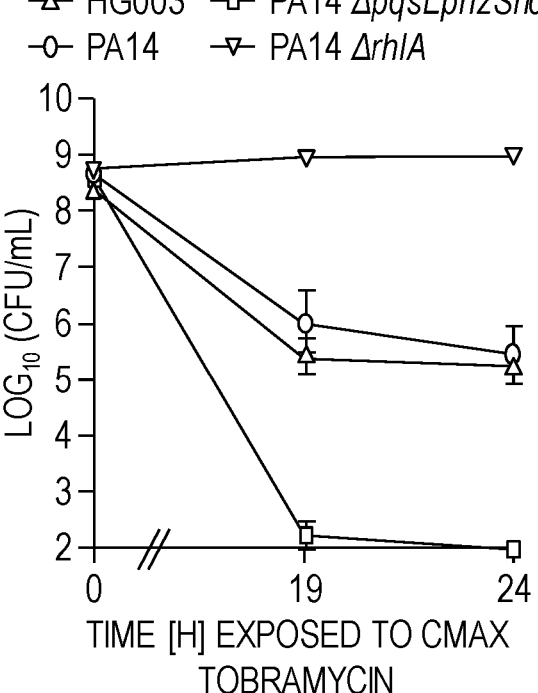
FIGS. 4A-4D show *P. aeruginosa* rhamnolipids potentiate aminoglycoside uptake and cell death in *S. aureus*. *S. aureus* HG003 was grown to mid-exponential phase and exposed to (A, B) sterile supernatants from *P. aeruginosa* or *S. aureus* or (C) exogenous addition of rhamnolipids 10-50 μg/ml before addition of tobramycin 58 μg/ml. At indicated times, an aliquot was washed and plated to enumerate survivors. (D) Texas Red-conjugated tobramycin was added to *S. aureus* cultures with or without 30 μg/ml rhamnolipids. Following 1 h, Texas Red-tobramycin uptake was measured by flow cytometry. Experiments were performed in biological triplicate. Error bars represent mean±sd.
Figure 4B:
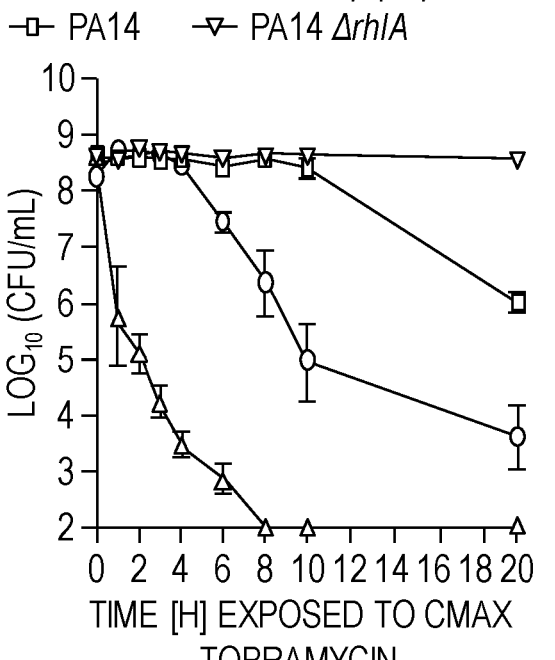
Figure 8A:
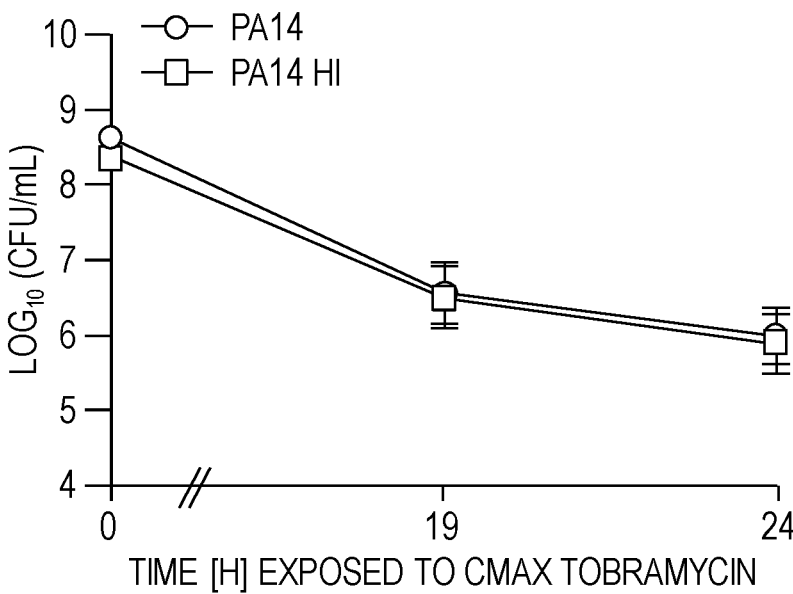
FIGS. 8A-8B show *S. aureus* strain HG003 was grown to mid-exponential phase in MHB media and pre-treated with (A) sterile supernatants from *P. aeruginosa* strains PA14, heat-inactivated PA14 (PA14 HI), or (B) exogenous rhamnolipids 10-50 μg/ml before addition of tobramycin at 58 μg/ml. At indicated times, an aliquot was washed and plated to enumerate survivors. All experiments were performed in biological triplicate. Error bars represent mean±sd.

Supernatant from both PAO1 and PA14 overnight cultures induce a 4- to 8-fold increase in the MIC of tobramycin, similar to previous reports (Table 1). Furthermore, exogenous addition of HQNO conferred full protection from tobramycin killing (FIG. 7D). Paradoxically, treatment with PAO1 or PA14 supernatant led to no significant induction of tobramycin tolerance in *S. aureus* (FIG. 1D). Strikingly, it was found that PA14 ΔpqsLphzShcnC mutant supernatant in conjunction with tobramycin treatment results in the rapid eradication of a *S. aureus* population (FIGS. 4A and 4B). Further, it was found that PA14 ΔpqsLphzShcnC supernatant reduced the MIC of tobramycin 2-fold relative to the control and 8- to 16-fold relative to PA14 treated *S. aureus* cells (Table 1). This suggests that an unknown factor present in *P. aeruginosa* supernatant is responsible for potentiating tobramycin killing. Heat-inactivation of *P. aeruginosa* supernatant did not induce tobramycin tolerance ruling out heat-labile proteins as possible potentiators of tobramycin killing (FIG. 8A).

Figure 4C:
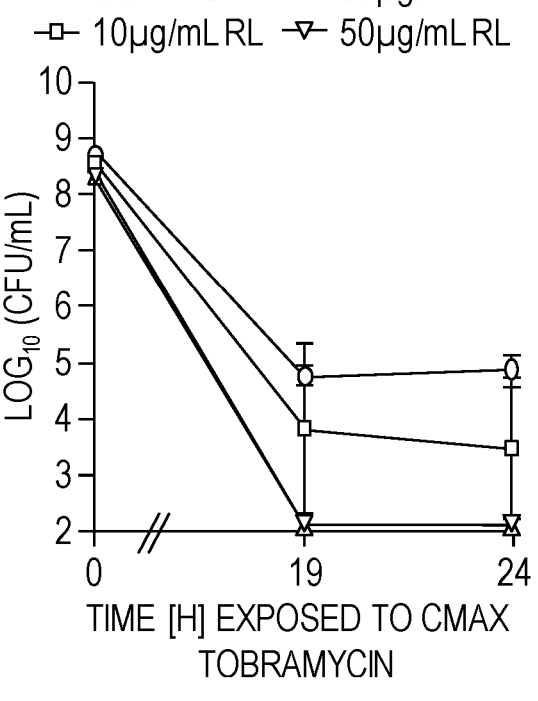
Figure 4D:
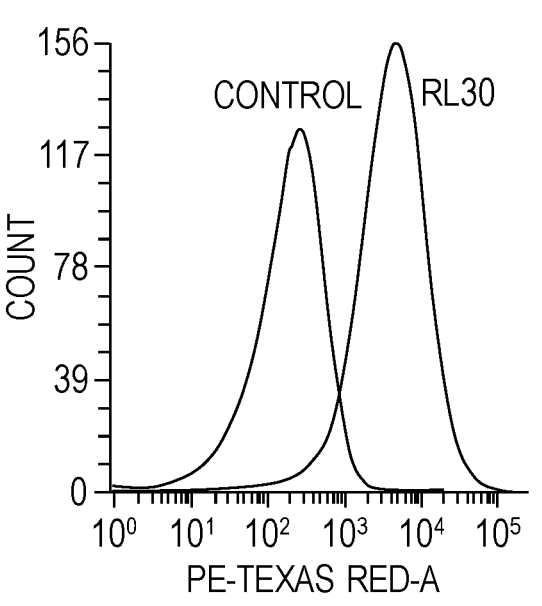
Figure 8B:
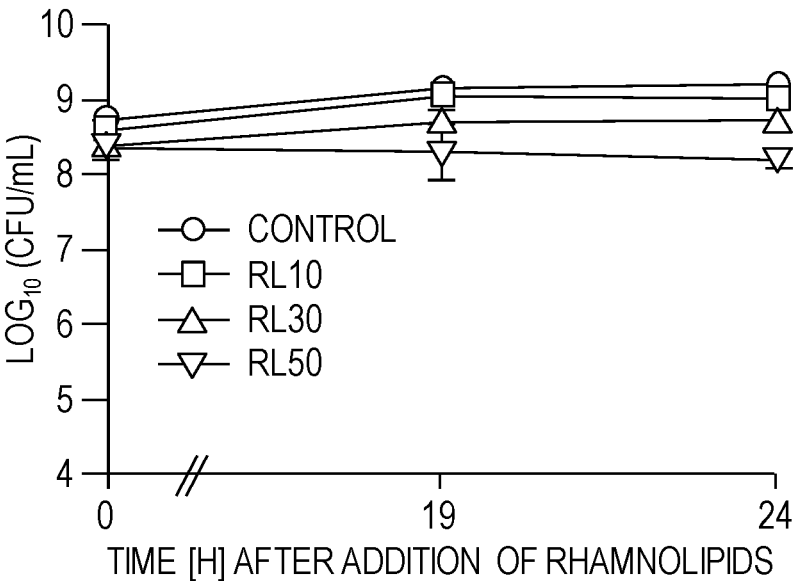

Tobramycin uptake is dependent on PMF. HQNO collapses *S. aureus* PMF by inhibiting electron transport, and thus abolishes tobramycin uptake into the cell. It was hypothesized that a potentiating agent may be able to induce tobramycin uptake in a PMF-independent manner. *P. aeruginosa* produces surfactant molecules called rhamnolipids that inhibit growth of competing Gram-positive bacteria and increase permeability by interacting with the plasma membrane. It was hypothesized that by increasing uptake in a PMF-independent manner, *P. aeruginosa* rhamnolipids may be potentiating tobramycin uptake in *S. aureus*. To investigate this possibility, a deletion was created in the rhlA gene in PA14, which is essential for rhamnolipid biosynthesis. Supernatant from a PA14 ΔrhlA mutant conferred full protection to *S. aureus* against tobramycin killing (FIGS. 4A and 4B). Furthermore, during tobramycin treatment, the exogenous addition of a 50-50 mix of purified *P. aeruginosa* mono- and di-rhamnolipids at a concentration of 30 and 50 μg/ml facilitated the rapid eradication of the *S. aureus* population (FIG. 4C). At these concentrations, rhamnolipids did not display bactericidal activity in the absence of antibiotic (FIG. 8B). It was found that at concentrations of 10, 30 and 50 μg/ml purified *P. aeruginosa* rhamnolipids reduced the MIC of tobramycin in *S. aureus* 2-, 4-, and 8-fold, respectively, (Table 1) and led to increased uptake of Texas Red-conjugated tobramycin as determined by flow cytometry (FIG. 4D). These data show that *P. aeruginosa* has the capacity to both positively and negatively influence *S. aureus* aminoglycoside uptake through the action of rhamnolipids and respiratory toxins, respectively. Furthermore, we demonstrate that low concentrations of purified rhamnolipids facilitate complete eradication of otherwise tolerant *S. aureus* persister populations in the presence of tobramycin. The remarkable ability of rhamnolipids to potentiate aminoglycoside killing, even in the absence of PMF, may be of major significance for antibiotic adjuvant development, and could lead to novel therapies with the capacity to eradicate recalcitrant *S. aureus* populations.

The Production of HQNO, LasA and Rhamnolipids is Highly Variable in *P. aeruginosa* Clinical Isolates

Figures 5A, 5B, 5C, 5D, 5E, 5F:
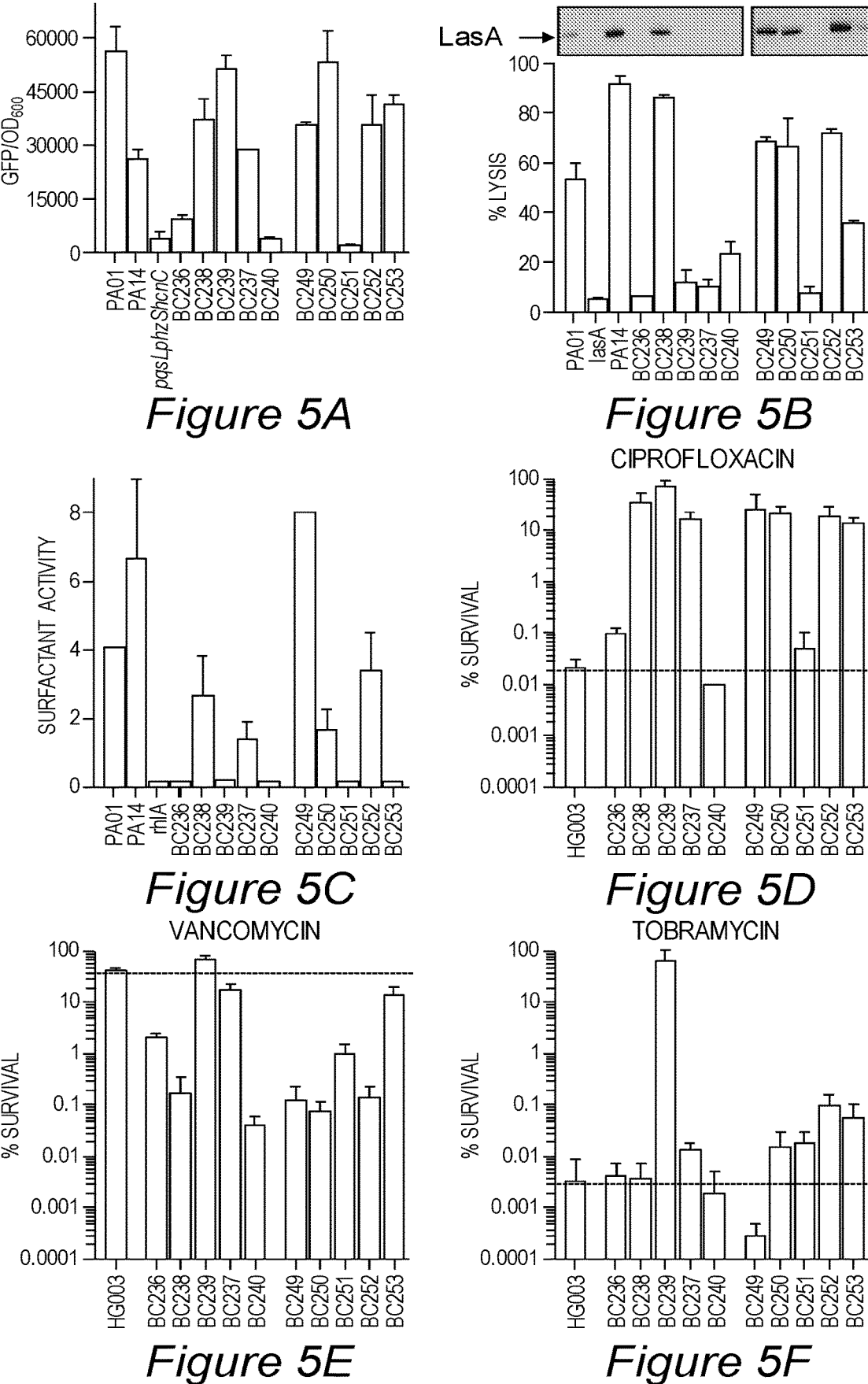
FIGS. 5A-5F show clinical *P. aeruginosa* isolates produce a wide range of antistaphylococcal factors and alter antibiotic tolerance in *S. aureus*. Antistaphylococcal factors present in the supernatant of *P. aeruginosa* CF isolates (blue) or burn isolates (green) were quantified as follows. (A) HQNO was measured by PpflB::gfp, reporter induction. (B) LasA was quantified by Western blot and the ability of each supernatant to lyse heat-killed *S. aureus* HG003 cells after 2 h. (C) Rhamnolipid production was measured by a drop-collapse assay. (D-F) *S. aureus* HG003 was grown to mid-exponential phase and exposed to sterile supernatants from clinical isolates or the control, *S. aureus* HG003 (red) for 30 min prior to addition of (D) ciprofloxacin (E) vancomycin or (F) tobramycin. An aliquot was removed after 24 h, washed and plated to enumerate survivors. All experiments were performed in biological triplicate, with the exception of (E) which was performed in biological duplicate. Error bars represent mean±sd.

*P. aeruginosa* potentiation and antagonism of antibiotic activity against *S. aureus* is complex and multifactorial. 5 *P. aeruginosa* isolates taken from CF lung infections and 5 *P. aeruginosa* isolates from acute burn wound infections were obtained. HQNO, LasA and rhamnolipid concentrations in the supernatant of each isolate were quantified then each isolate's capacity to alter *S. aureus* antibiotic susceptibility was examined. As HQNO-mediated inhibition of *S. aureus* respiration induces the expression of pflB (FIG. 2A), a PpflB::gfp, reporter was used to measure relative HQNO levels in *P. aeruginosa* supernatants (FIG. 5A). In addition, HQNO production by these isolates was directly quantified through mass spectrometry (Table 2). LasA expression was quantified by Western blot as well as by the capacity of each supernatant to lyse a culture of heat-killed *S. aureus* (Figure Rhamnolipids were measured by drop collapse assay, a qualitative measurement of biosurfactant activity (FIG. 5C). It was found that the production of each of these factors is highly variable between clinical isolates (FIGS. 5A-5C). As these molecules have a dramatic impact on *S. aureus* antibiotic susceptibility, this variance may be an important factor in determining the outcome of antibiotic treatment.

Interestingly, 8 of 10 isolates were capable of inducing protection from ciprofloxacin killing and this correlated perfectly with HQNO levels in the supernatant as well as the induction of our PpflB::gfp, reporter (FIGS. 5A and 5D) (Table 2). Similarly, of the 8 supernatants that stimulated at least a 10-fold potentiation of vancomycin killing, 6 were positive for LasA, as measured by Western blot, lytic assay or both (FIGS. 5B and 5E). BC236 and BC251 potentiated vancomycin killing in the absence of apparent LasA activity. These strains may produce LasA at levels below the limit of detection or may potentiate vancomycin through an unidentified mechanism. Of note, neither of these strains produced detectable levels of HQNO, which is inhibitory of vancomycin killing (Table 2).

CF isolate BC239 was a high producer of HQNO and did not produce rhamnolipids. In agreement with these findings, supernatant from this isolate conferred marked protection in *S. aureus* against tobramycin killing (FIGS. 5A, 5C, and 5F) (Table 2). Conversely, supernatant from strain BC249, a burn isolate and the highest rhamnolipid producer examined, increased killing by tobramycin approximately 10-fold (FIGS. 5C and 5F).

DISCUSSION

Figure 6:
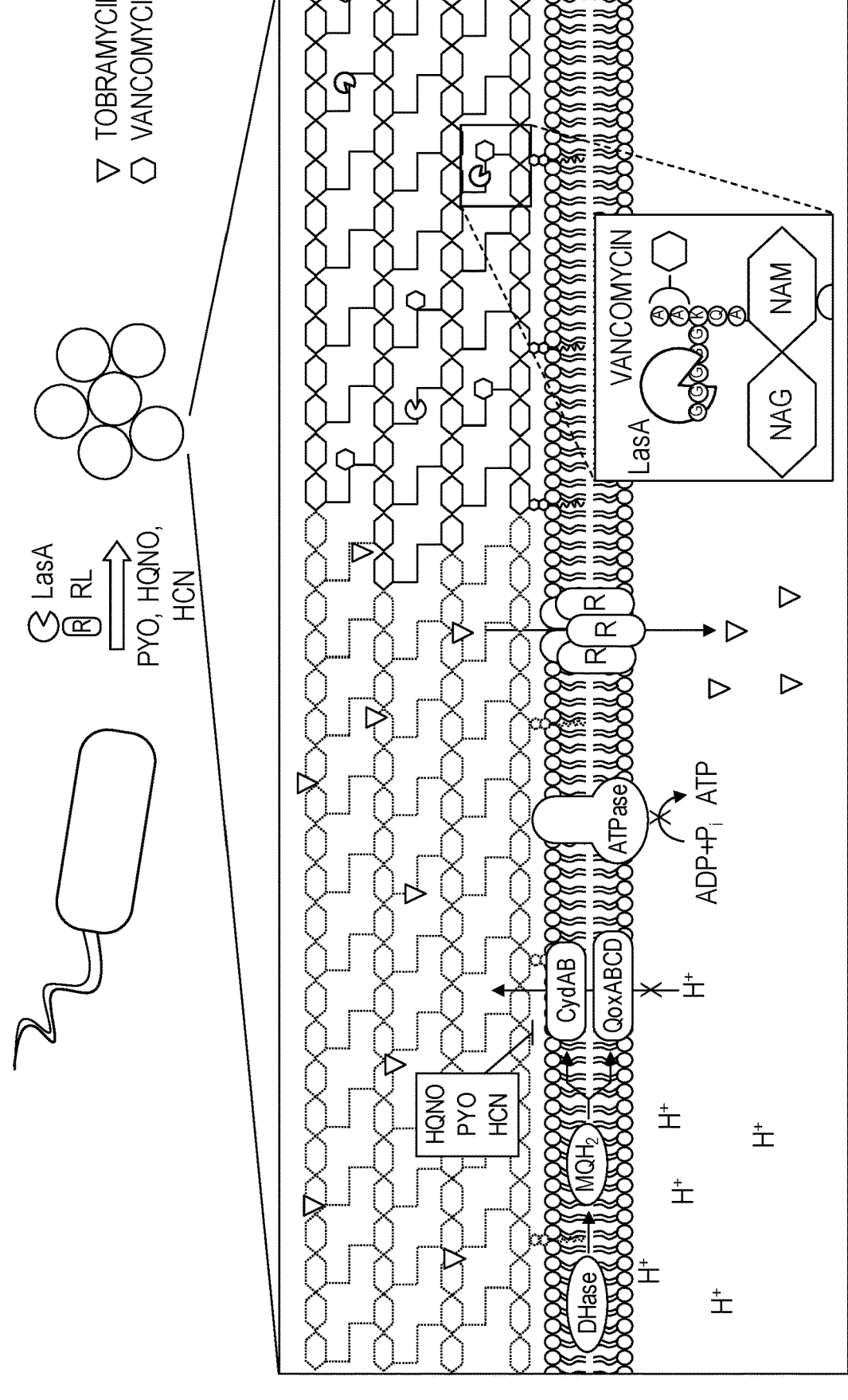
FIG. 6 shows *P. aeruginosa* mediated alteration of *S. aureus* antibiotic susceptibility. *P. aeruginosa* exoproducts pyocyanin (PYO), 2-heptyl-4-hydroxyquinoline N-oxide (HQNO), and hydrogen cyanide (HCN) inhibit *S. aureus* electron transport, leading to collapse of proton-motive force (PMF) and inhibition of the $F_1F_0$ ATPase leading to a decrease in *S. aureus* antibiotic susceptibility. Conversely, *P. aeruginosa* rhamnolipids (RL) intercalate into the plasma membrane forming pores that permit aminoglycoside entry into the cell in a PMF-independent manner. Finally, *P. aeruginosa* endopeptidase LasA cleaves pentaglycine cross-links between peptidoglycan molecules of the cell wall, increasing vancomycin-mediated lysis of *S. aureus*.

During such co-infections, *P. aeruginosa* employs an arsenal of weaponry to compete with *S. aureus*. A model is proposed whereby antibiotic efficacy against *S. aureus* is determined by interactions with co-infecting *P. aeruginosa* (FIG. 6). In support of this, it was demonstrated that HQNO-mediated inhibition of respiration forces *S. aureus* into a low ATP, multidrug tolerant state. It was further demonstrated that the presence of LasA in *P. aeruginosa* supernatant is sufficient to override this protective effect, and instead potentiates vancomycin-mediated cell lysis and death. Similarly, though HQNO mediates *S. aureus* resistance to tobramycin, it was shown that *P. aeruginosa*-produced rhamnolipids can negate this effect and restore or even increase *S. aureus* susceptibility to tobramycin killing. Stimulating tobramycin uptake has been proposed as a way to eradicate persister populations. The present data suggest that rhamnolipids facilitate penetration of tobramycin independently of proton-motive force. Exogenous addition of rhamnolipids to *S. aureus* cultures resulted in dramatic potentiation of tobramycin killing, leading to total eradication of *S. aureus* persister populations. Further exploitation of LasA and rhamnolipid-mediated antibiotic potentiation could lead to future antibiotic adjuvants that facilitate eradication of recalcitrant *S. aureus* populations for the treatment of chronic infection.

It was found that the capacity of clinical *P. aeruginosa* isolates to antagonize or potentiate the killing activities of antibiotics against *S. aureus* is highly variable and dependent on the production of antistaphylococcal compounds. The production of HQNO, LasA and rhamnolipids are regulated by quorum sensing (QS) in *P. aeruginosa*. *P. aeruginosa* frequently accumulates mutations in genes required for QS during chronic infection. Interestingly, in support of this, strains from acute burn wound infections appear to produce higher levels of HQNO, LasA and rhamnolipids, while isolates from CF lung infections tended to produce less of these compounds. The diversity of HQNO, LasA and rhamnolipid production by *P. aeruginosa* clinical isolates and their impact on *S. aureus* suggests that genotypic variation of *P. aeruginosa* may have a significant impact on antibiotic susceptibility of *S. aureus* during co-infection. It will be interesting to measure the levels of these antistaphylococcal factors in a larger clinical strain cohort in future studies.

TABLE 1

| | | | | |
|---|---|---|---|---|
| Minimum inhibitory concentrations (MIC) of *S. aureus* HG003 | | | | |
| Antibiotic | Control | +HG003 supernatant | PAO1 and PA14 supernatant | PA14 ΔpqsLphzShcnC |
| MIC ciprofloxacin (µg/ml) | 0.3 | 0.3 | 0.3 | — |
| MIC tobramycin (µg/ml) | 0.78 | 0.78 | 3.125-6.25 | 0.39 |
| MIC oxacillin (µg/ml) | 0.39 | 0.39 | 0.39 | — |
| MIC vancomycin (µg/ml) | 1.25 | 1.25 | 1.25 | — |
| Antibiotic | Control | 10 µg/ml rhamnolipids | 30 µg/ml rhamnolipids | 50 µg/ml rhamnolipids |
| MIC tobramycin (µg/ml) | 0.78 | 0.39 | 0.195 | 0.0975 |

TABLE 2

| | |
|---|---|
| LC-MS/MS quantification of HQNO production in *P. aeruginosa* strains | |
| Strain | Conc. (µM) |
| PAO1 | 31.5 |
| PA14 | 28.3 |
| PA14 ΔpqsL | ND |
| BC236 | ND |
| BC237 | 18.9 |
| BC238 | 13.9 |
| BC239 | 25.7 |
| BC240 | ND |
| BC249 | 29.0 |
| BC250 | 28.2 |
| BC251 | ND |
| BC252 | 47.0 |
| BC253 | 9.8 |

Example 2

Effect of Tobramycin and Rhamnolipids on Biofilms

Figure 9:
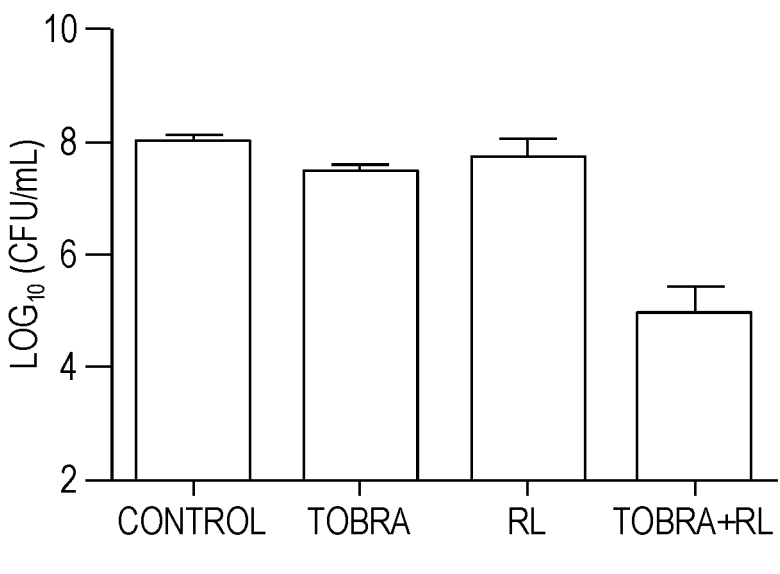
FIG. 9 shows biofilm killing using tobramycin and rhamnolipids.

For biofilm killing assays, *S. aureus* was grown in 96-well polystyrene plates in Tryptic Soy Broth (TSB) overnight. Media was removed and biofilm formed on the base of the plates was washed 3 times in sterile PBS. Fresh media containing tobramycin alone, rhamnolipids alone or a combination was added and plates were incubated overnight. Media was removed. Biofilm was washed 3 times. Sterile PBS was added to each well and plates were placed in a sonicating water bath for 10 minutes to remove the biofilm from the plate. PBS containing solubilized biofilm was then serially diluted and plated on MHA plates to enumerate survivors. The results are shown in FIG. 9.

Example 3

Effect of Tobramycin and Rhamnolipids on Anaerobic Killing

Figure 10:
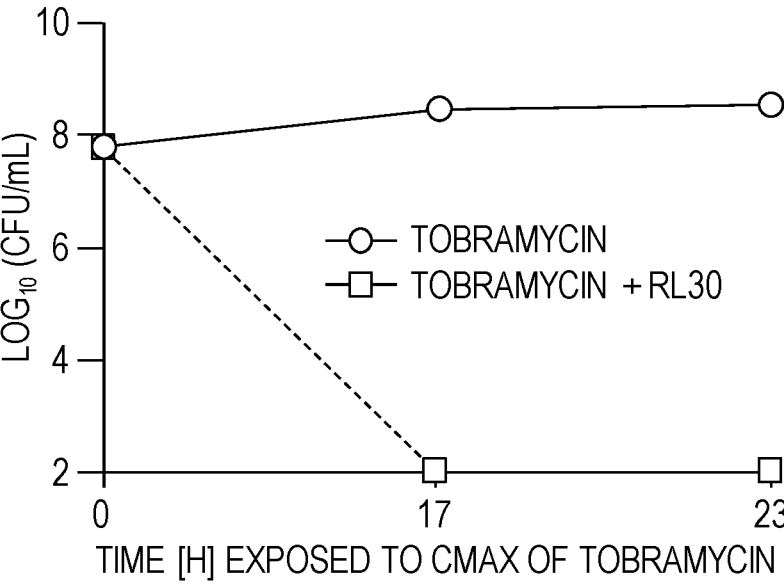
FIG. 10 shows anaerobic killing using tobramycin and rhamnolipids.

For anaerobic killing assays, *S. aureus* was grown in MHB in an anaerobic chamber to mid-exponential phase. Tobramycin, rhamnolipids and a combination of the two were then added to cultures and the cultures were incubated anaerobically overnight. Cultures were then centrifuged and cells were washed, serially diluted and plated for survivors. The results are shown in FIG. 10.

Example 4

Effect of Tobramycin and Rhamnolipids on *S. aureus*

Figure 11:
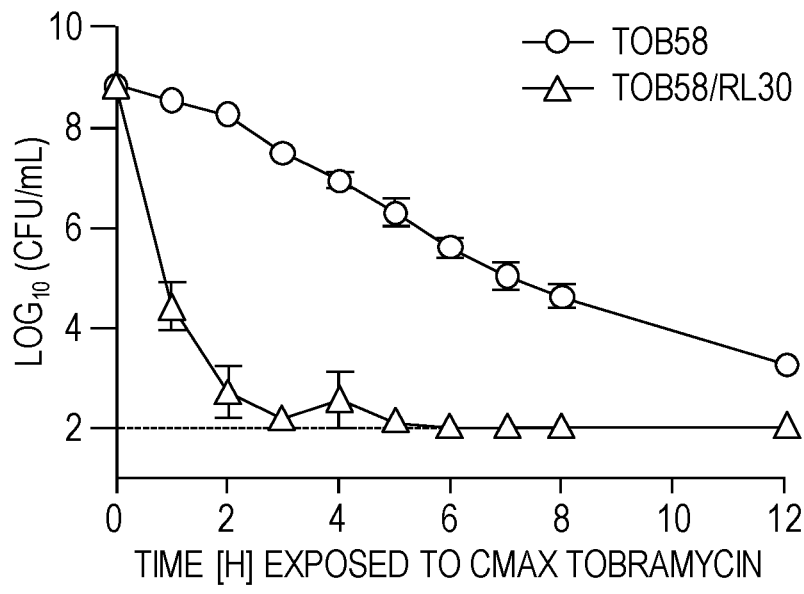
FIG. 11 shows rhamnolipids at 30 μg/ml potentiates killing of *S. aureus* HG003 by tobramycin.

The ability of rhamnolipids to potentiate killing of *S. aureus* by tobramycin was examined. *S. aureus* HG003 was grown in MHB for 3 hours 30 minutes and then challenged with tobramycin at 58 µg/ml alone or in combination with 30 µg/ml rhamnolipids. The combination showed eradication of the population within 5 hours while the use of tobramycin alone resulted in $10^4$ survivors even after 12 hours (FIG. 11).

Example 5

Figure 12:
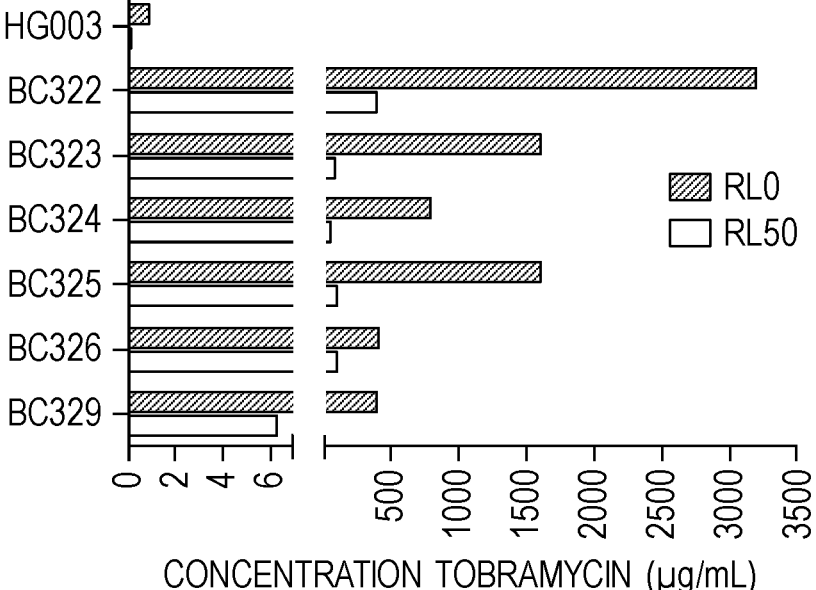
FIG. 12 shows rhamnolipids at 50 μg/ml dramatically reduces the MIC of tobramycin against a variety of tobramycin resistant clinical isolates taken from cystic fibrosis patients' lungs.

Effect of Tobramycin and Rhamnolipids on Tobramycin Resistant *S. aureus* Isolates Tobramycin resistant *S. aureus* isolates were cultured from the sputum of 6 cystic fibrosis patients. MIC experiments were performed with tobramycin in MHB. MIC experiments were then repeated in the presence of 50 µg/ml rhamnolipids. Rhamnolipids reduced the MIC significantly (FIG. 12).

Example 6

Effect of Tobramycin and Rhamnolipids on Low Energy *S. aureus*

Figures 13, 14:
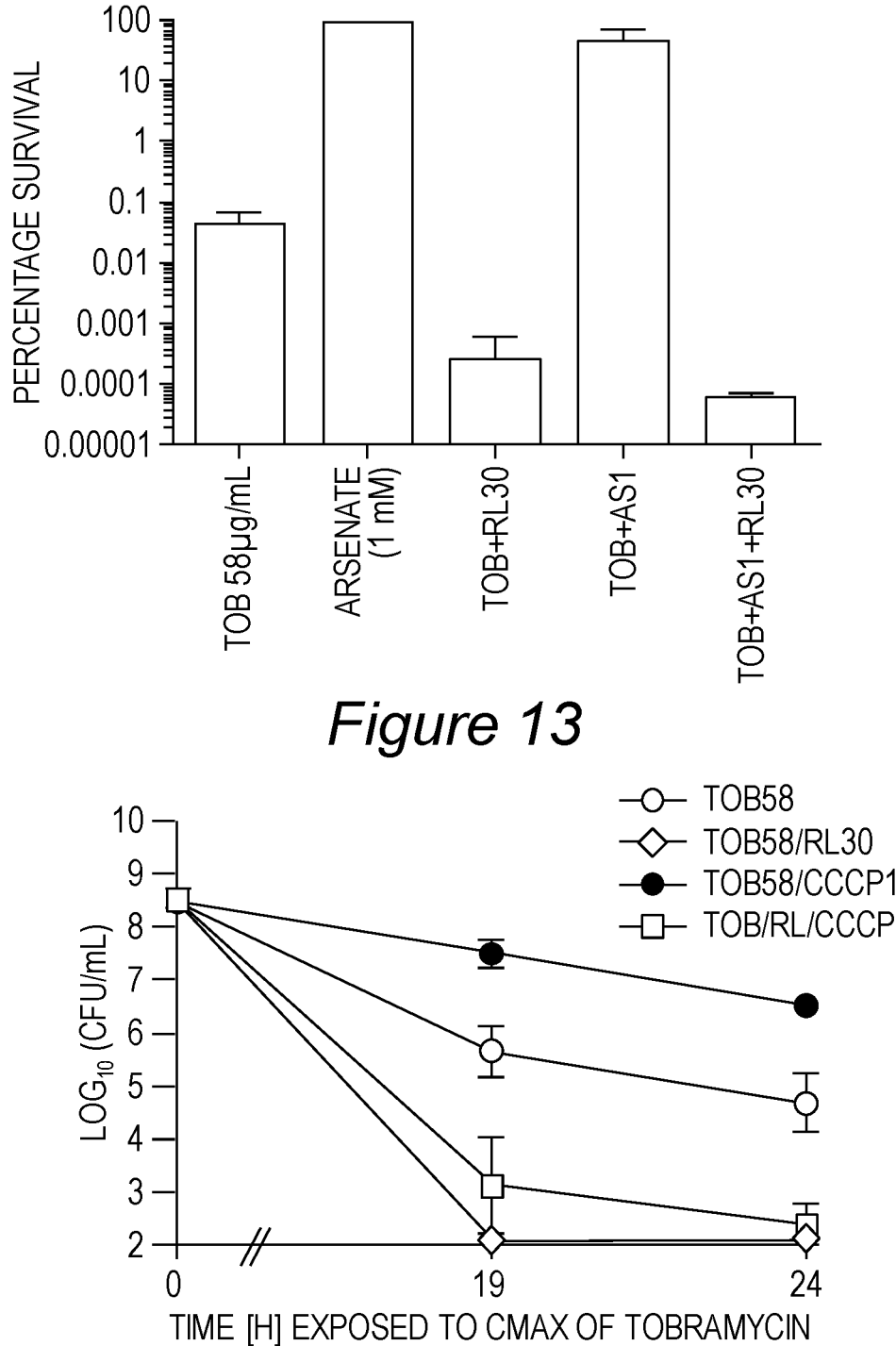
FIG. 13 shows rhamnolipids sensitize low energy (arsenate treated) *S. aureus* to tobramycin killing.
FIG. 14 shows rhamnolipids sensitize *S. aureus* to tobramycin in the presence of CCCP which collapses membrane potential and classical tobramycin uptake.

*S. aureus* HG003 was grown to late exponential phase, to which was added tobramycin alone at 58 µg/ml, arsenate alone at 1 mM, arsenate in combination with tobramycin, and arsenate, tobramycin and rhamnolipids (at 30 µg/ml). cfu/ml were quantified before addition and after 24 hours, when survivors were enumerated (FIG. 13).

It was previously shown that *S. aureus* reaches an antibiotic tolerant state by maintaining a low intracellular ATP concentration. Low ATP can be induced artificially using arsenate. Under these conditions, tobramycin fails to kill *S. aureus*. However, in the presence of rhamnolipids, even this reduction in ATP is not protective and the population is reduced by 6 logs over 24 hours. The low energy state is thought to be highly relevant in vivo where nutrient limitation occurs and cells maintain a far slower growth rate than in vitro.

Example 7

Effect of Tobramycin and Rhamnolipids on CCCP-Treated *S. aureus*

*S. aureus* HG003 was grown to exponential phase, to which was added tobramycin (58 μg/ml) alone or in combination with carbonyl cyanide m-chlorophenyl hydrazine (CCCP; 1 μg/ml) or rhamnolipids (30 μg/ml). Survivors were enumerated after 19 hours and 24 hours (FIG. 14).

CCCP collapses the membrane potential and inhibits tobramycin uptake and cell death. Even in the presence of CCCP, rhamnolipids can induce uptake of tobramycin and killing of the *S. aureus* population.

Example 8

Effect of Protein Synthesis Inhibitors on Tobramycin and Rhamnolipids-Mediated Killing of *S. aureus*

Figure 15:
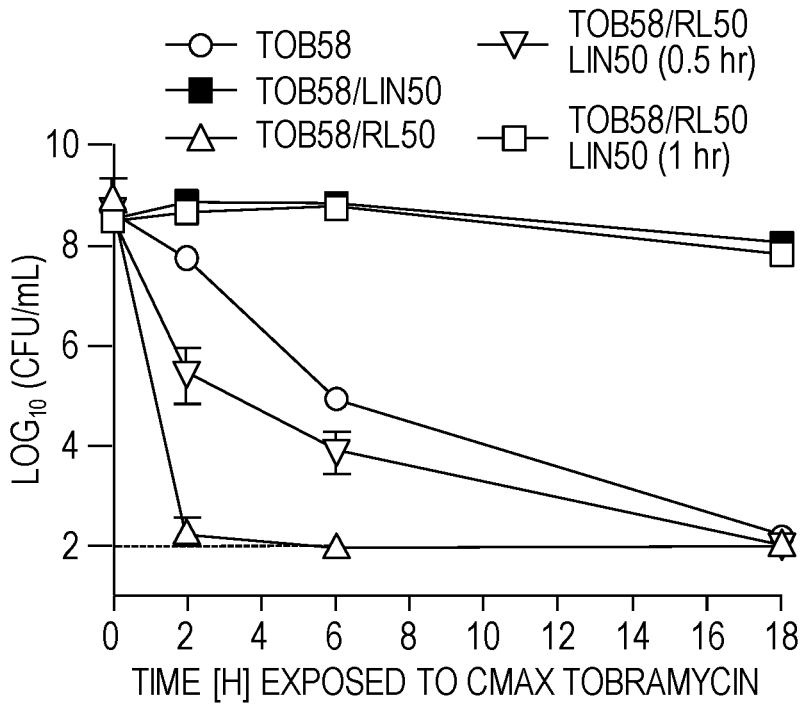
FIG. 15 shows protein synthesis inhibition inhibits tobramycin killing but does not inhibit tobramycin mediated killing in the presence of rhamnolipids.

*S. aureus* HG003 was grown in MHB for 3 hours 30 minutes and then challenged with tobramycin at 58 μg/ml alone or in combination with 50 μg/ml of linezolid (added 1 hour before), 50 μg/ml rhamnolipids or both. Survivors were enumerated at various timepoints (FIG. 15).

During conditions where protein synthesis is low or inhibited, tobramycin fails to kill as is seen in the tobramycin/linezolid combination experiment. This is important as an array of physiologically relevant conditions will result in low protein synthesis rates relative to those seen under ideal conditions in vitro. Importantly, even in the presence of linezolid, a combination of tobramycin and rhamnolipids is capable of inducing cell death, while tobramycin alone fails to kill.

Example 9

Effect of Tobramycin and Rhamnolipids on Development of Tobramycin-Resistant *S. aureus*

Figure 16:
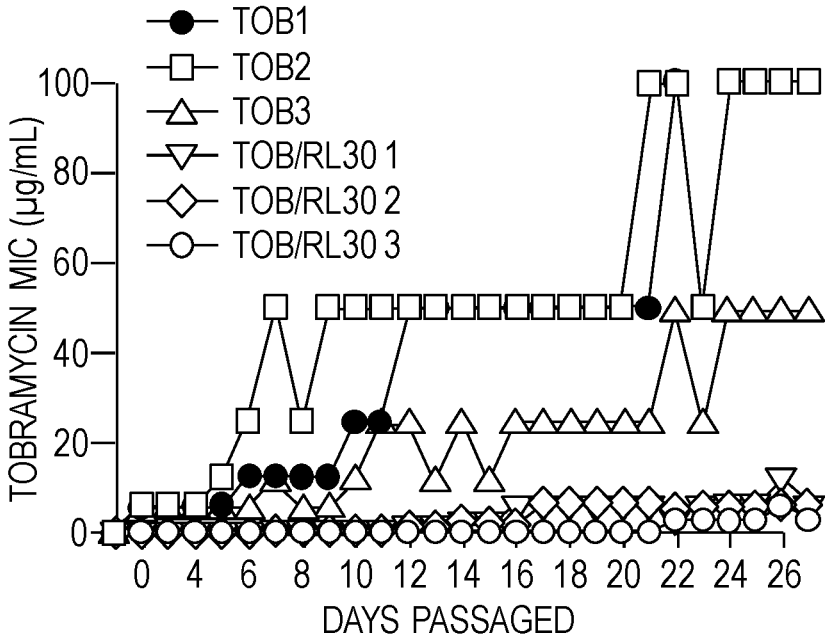
FIG. 16 shows sub-culturing *S. aureus* in increasing concentrations of tobramycin results in swift selection for highly resistant isolates. However, no selection for highly resistant isolates occurs in the presence of rhamnolipids.

*S. aureus* was sub-cultured in increasing concentrations of tobramycin in the presence or absence of rhamnolipids. MIC experiments were performed daily, with the bacteria growing in the highest concentration of antibiotic used as the inoculum for the next MIC. This procedure selects for the bacteria most capable of growing in the antibiotic. For 3 separate experiments, high level resistance to tobramycin was selected for by day 10 and it increased as high as 100 μg/ml by day 26 (FIG. 16). This high level resistance is similar to that observed in isolates from cystic fibrosis patients lungs. Interestingly, in the presence of 30 μg/ml rhamnolipids, resistance does not develop, even after 27 days of sub-culture.

Example 10

Effect of Tobramycin and Rhamnolipids on a Small Colony Variant of *S. aureus*

Figure 17:
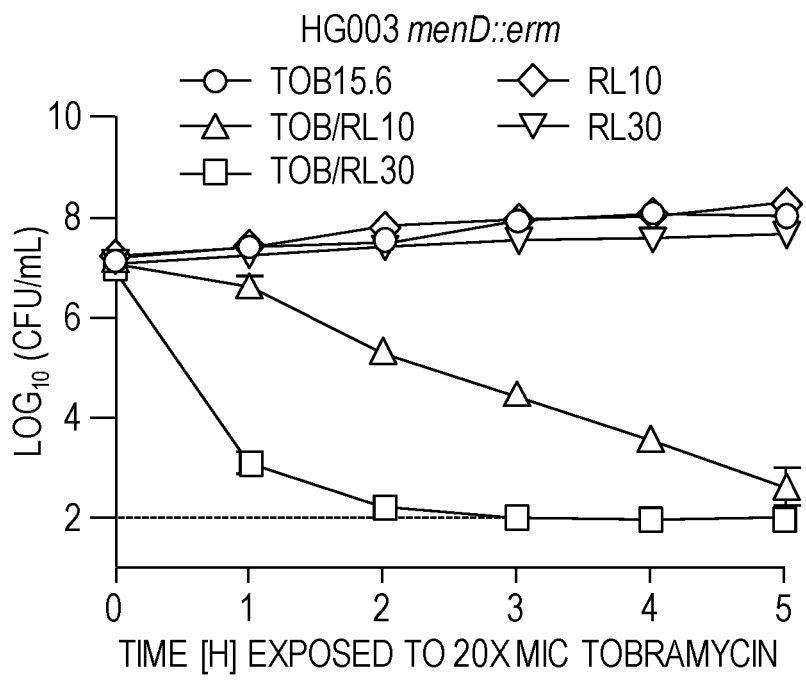
FIG. 17 shows small colony variant (SCV) of *S. aureus*, HG003 menD::erm, is resistant to tobramycin but in the presence of rhamnolipids can be killed by tobramycin.

A menD mutant was constructed in *S. aureus* HG003. This mutant grows slowly and is resistant to tobramycin due to a collapse in membrane potential. The mutant was grown to exponential phase and tobramycin was added alone or in combination with rhamnolipids at 10 μg/ml or 30 μg/ml (FIG. 17). Rhamnolipids sensitized the small colony variant to tobramycin and at 30 μg/ml facilitated eradication to limit of detection within 2 hours. SCVs are highly physiologically relevant and very difficult to kill with conventional antibiotics. These data suggest that combining antibiotic with rhamnolipids will facilitate rapid eradication of small colony variants.

Figure 18:
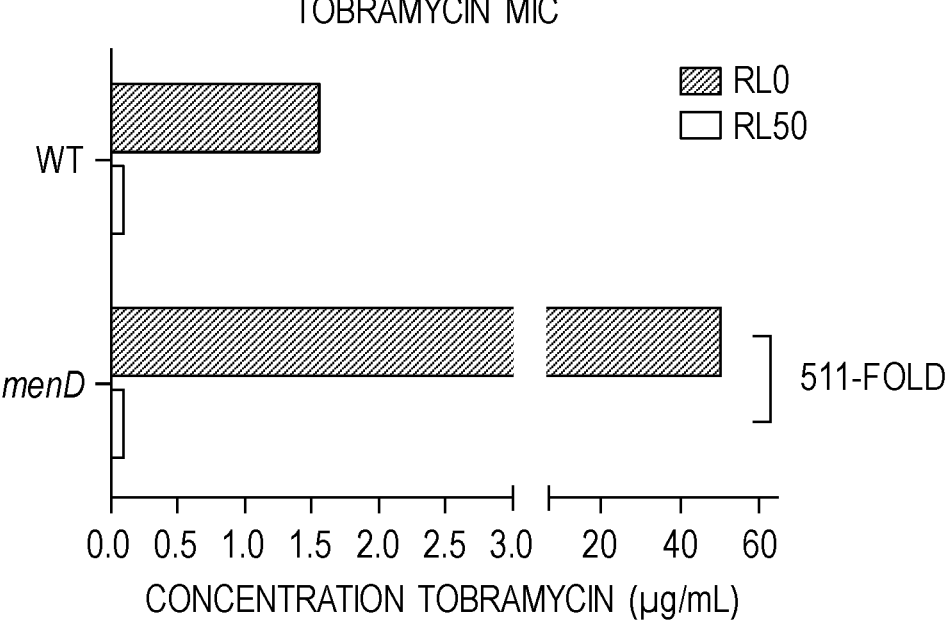
FIG. 18 shows rhamnolipids cause a 511-fold collapse in the MIC of SCV strain to tobramycin.

MIC experiments were carried out with the menD mutant in MH broth. It was found that addition of rhamnolipids at 50 μg/ml resulted in a 511 fold reduction in MIC of the SCV to tobramycin (FIG. 18).

Example 11

Effect of Rhamnolipids and Other Membrane-Permeabilizing Molecules on *S. aureus*

Figure 19A:
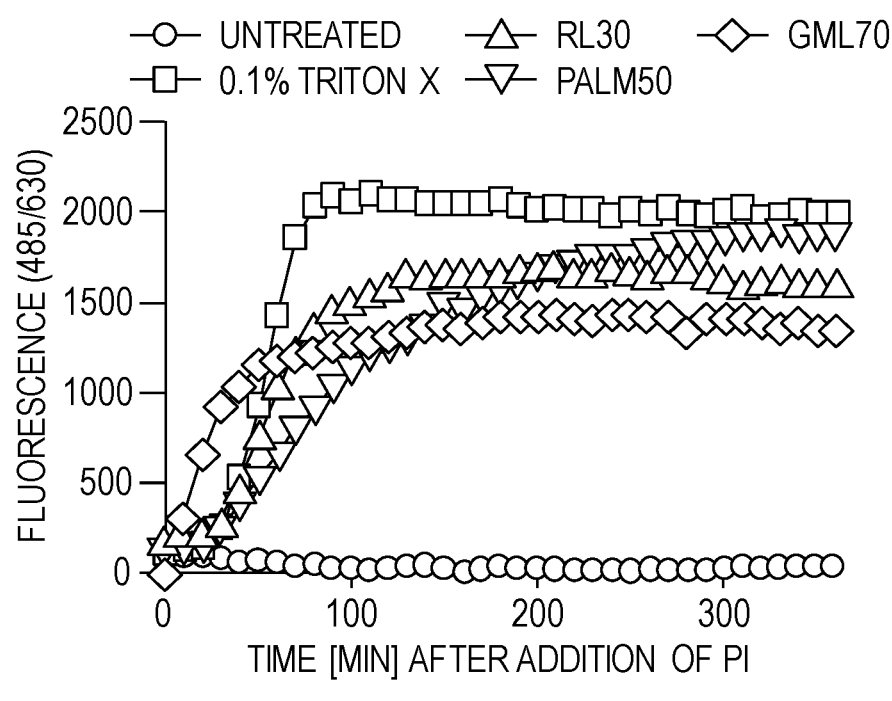
FIGS. 19A-19B show other membrane permeabilizing molecules also synergize with tobramycin. (A) Propidium iodide uptake experiments confirmed that palmitoleic acid (Palm50) and glycerol monolaureate (GML) permeabilize *S. aureus*. (B) Killing experiments with tobramycin showed significant potentiation of tobramycin killing over 24 hours.
Figure 19B:
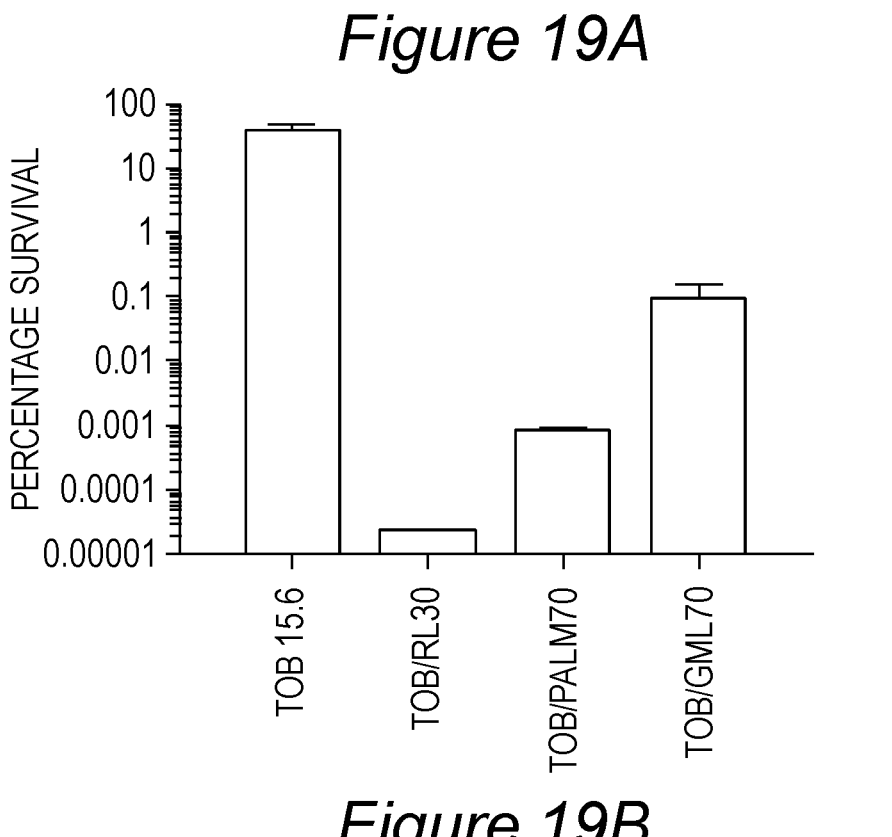

*S. aureus* HG003 was grown to exponential phase in a 96 well plate. Rhamnolipids, palmitoleic acid (Palm50), and glycerol monolaureate (GML) were added. These concentrations were not lethal to *S. aureus* alone. Propidium iodide (PI) was then added to measure the permeability of the *S. aureus* membrane (FIG. 19A). PI only fluoresces when it penetrates the cell and under normal conditions, PI will not penetrate live bacteria. When the membrane is compromised, PI can enter. The ability of these permeabilizing molecules in combination with tobramycin to kill *S. aureus* over 24 hours was quantitated (FIG. 19B). The data show that other membrane-permeabilizing surfactants can synergize with tobramycin to permeabilize *S. aureus*. An array of other chemicals known to permeabilize the *S. aureus* membrane were found to potentiate aminoglycoside killing of *S. aureus*.

Example 12

Effect of Different Rhamnolipids on Potentiation of Tobramycin

Figure 20:
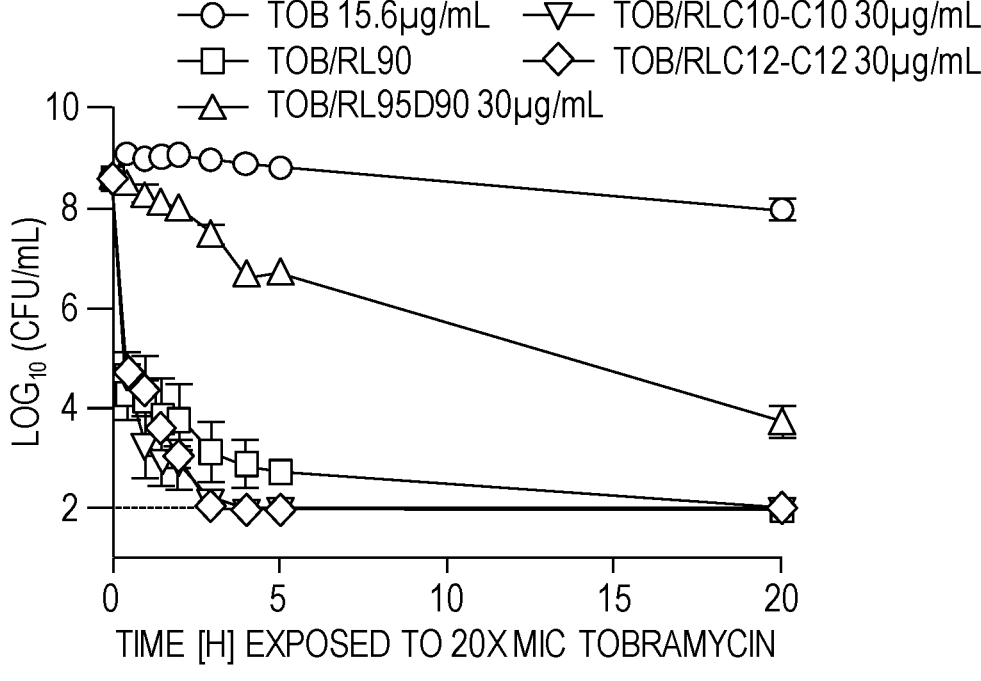
FIG. 20 shows the effect of different rhamnolipids on potentiation of tobramycin.

Various rhamnolipids were added to *S. aureus* HG003 in combination with tobramycin at 15.6 μg/ml (equivalent to 20 times the minimum inhibitory concentration). RL90 is a mix of rhamnolipids containing mono- and di-rhamnolipids with different carbon chain lengths. RL95D90 is 95% pure rhamnolipids, and 90% di-rhamnolipid. RLC10-C10 is pure mono-rhamnolipid with 2 C10 carbon tails. RLC12-C12 is pure mono-rhamnolipid with 2 C12 carbon tails. All rhamnolipids tested could potentiate tobramycin killing with the di-rhamnolipid dominant rhamnolipids displaying less activity than mono-rhamnolipids (FIG. 20).

The foregoing is illustrative of the present invention, and is not to be construed as limiting thereof. The invention is defined by the following claims, with equivalents of the claims to be included therein.

That which is claimed is:

1. A method of treating a bacterial infection comprising a biofilm in a subject in need thereof, comprising administering to the subject a therapeutically effective amount of a surfactant and at least one of an aminoglycoside antibiotic or vancomycin, wherein:

(a) the surfactant consists of palmitoleic acid;

(b) the aminoglycoside antibiotic comprises streptomycin, kanamycin A, amikacin, dibekacin, sisomicin, netilmicin, neomycin B, neomycin C, neomycin E, or any combination thereof;

(c) the surfactant synergizes with the aminoglycoside antibiotic or vancomycin to decrease the minimum inhibitory concentration (MIC) of the aminoglycoside antibiotic or vancomycin;

wherein the bacterial infection comprising a biofilm is caused by gram-positive bacteria; and wherein the bacterial infection comprising a biofilm is treated.

2. A method of reducing the risk of recurrence of a bacterial infection in a subject in need thereof, comprising administering to the subject having a bacterial infection comprising a biofilm a therapeutically effective amount of a surfactant and at least one of an aminoglycoside antibiotic or vancomycin, wherein:

(a) the surfactant consists of palmitoleic acid;

(b) the aminoglycoside antibiotic comprises streptomycin, kanamycin A, amikacin, dibekacin, sisomicin, netilmicin, neomycin B, neomycin C, neomycin E, or any combination thereof;

(c) the surfactant synergizes with the aminoglycoside antibiotic or vancomycin to decrease the MIC of the aminoglycoside antibiotic or vancomycin;

wherein the bacterial infection comprising a biofilm is caused by a gram-positive bacteria; and wherein the risk of recurrence of a bacterial infection is reduced.

3. A method of disrupting a biofilm, comprising contacting the biofilm with an effective amount of a surfactant and at least one of an aminoglycoside antibiotic or vancomycin, wherein:

(a) the surfactant consists of palmitoleic acid;

(b) the aminoglycoside antibiotic comprises streptomycin, kanamycin A, amikacin, dibekacin, sisomicin, netilmicin, neomycin B, neomycin C, neomycin E, or any combination thereof;

(c) the surfactant synergizes with the aminoglycoside antibiotic or vancomycin to decrease the MIC of the aminoglycoside antibiotic or vancomycin;

wherein the biofilm is from a gram-positive bacteria; and wherein the biofilm is disrupted.

4. The method of claim 1, wherein the bacteria is antibiotic resistant or antibiotic tolerant.

5. The method of claim 1, wherein the bacteria is *Staphylococcus aureus*.

6. The method of claim 5, wherein the bacteria is methicillin-resistant *Staphylococcus aureus*.

7. The method of claim 1, wherein the surfactant and the aminoglycoside antibiotic or vancomycin are administered simultaneously.

8. The method of claim 1, wherein the surfactant and the aminoglycoside antibiotic or vancomycin are administered sequentially.

9. The method of claim 2, wherein the bacteria is antibiotic resistant or antibiotic tolerant.

10. The method of claim 2, wherein the bacteria is *Staphylococcus aureus*.

11. The method of claim 10, wherein the bacteria is methicillin-resistant *Staphylococcus aureus*.

12. The method of claim 2, wherein the surfactant and the aminoglycoside antibiotic or vancomycin are administered simultaneously.

13. The method of claim 2, wherein the surfactant and the aminoglycoside antibiotic or vancomycin are administered sequentially.

14. The method of claim 3, wherein the bacteria is antibiotic resistant or antibiotic tolerant.

15. The method of claim 3, wherein the bacteria is *Staphylococcus aureus*.

16. The method of claim 15, wherein the bacteria is methicillin-resistant *Staphylococcus aureus*.

17. The method of claim 3, wherein the surfactant and the aminoglycoside antibiotic or vancomycin are administered simultaneously.

18. The method of claim 3, wherein the surfactant and the aminoglycoside antibiotic or vancomycin are administered sequentially.

* * * * *